(12) United States Patent
Harvie et al.

(10) Patent No.: US 6,620,185 B1
(45) Date of Patent: Sep. 16, 2003

(54) SURGICAL PROCEDURES AND INSTRUMENTS

(75) Inventors: Fraser Harvie, East Kilbride (GB); Adam James, Talbot Green (GB); Peter Richardson, Arlington, MA (US); James William Huckle, Northallerton (GB)

(73) Assignee: Smith & Nephew, Inc., Andover, MA (US)

( * ) Notice: Subject to any disclaimer, the term of this patent is extended or adjusted under 35 U.S.C. 154(b) by 260 days.

(21) Appl. No.: 09/604,387

(22) Filed: Jun. 27, 2000

(51) Int. Cl.[7] .............................................. A61B 17/04
(52) U.S. Cl. ........................ 606/232; 606/215; 606/92
(58) Field of Search ............................ 606/72, 92, 93, 606/215, 216, 219, 220, 232

(56) References Cited

U.S. PATENT DOCUMENTS

| | | | |
|---|---|---|---|
| 4,200,939 A | * | 5/1980 | Oser |
| 4,532,661 A | * | 8/1985 | Halpern .................. 623/23 |
| 4,585,458 A | * | 4/1986 | Kurland .................. 623/13 |
| 4,595,713 A | | 6/1986 | St. John ................. 523/105 |
| 4,645,503 A | | 2/1987 | Lin et al. ................ 623/16 |
| 4,702,236 A | * | 10/1987 | Tarabichy et al. |
| 4,843,112 A | * | 6/1989 | Gerhart et al. ........... 523/114 |
| 5,250,055 A | | 10/1993 | Moore et al. ............. 606/148 |
| 5,397,572 A | | 3/1995 | Coombes et al. .......... 424/426 |
| 5,433,751 A | | 7/1995 | Christel et al. ........... 623/16 |
| 5,441,502 A | * | 8/1995 | Bartlett ................. 606/104 |
| 5,482,717 A | | 1/1996 | Fues et al. .............. 424/426 |
| 5,486,593 A | | 1/1996 | Tang et al. .............. 528/370 |
| 5,620,700 A | | 4/1997 | Berggren et al. ........... 424/435 |
| 5,641,502 A | | 6/1997 | Skalla et al. ............. 424/426 |
| 5,649,959 A | * | 7/1997 | Hannam et al. ............ 606/213 |
| 5,665,110 A | | 9/1997 | Chervitz et al. ........... 606/232 |
| 5,665,111 A | * | 9/1997 | Ray et al. ................ 606/232 |
| 5,679,723 A | | 10/1997 | Cooper et al. ............ 523/115 |
| 5,681,873 A | | 10/1997 | Norton et al. ............ 523/115 |
| 5,683,419 A | * | 11/1997 | Thal ..................... 606/232 |
| 5,735,875 A | * | 4/1998 | Bonutti et al. ............ 606/232 |
| 5,753,781 A | | 5/1998 | Oxman et al. ............. 525/415 |
| 5,824,333 A | | 10/1998 | Scopelianos et al. ........ 424/423 |
| 5,893,856 A | * | 4/1999 | Jacob et al. .............. 606/151 |
| 5,925,036 A | | 7/1999 | Maxwell, III .............. 606/13 |
| 5,928,239 A | * | 7/1999 | Mirza .................... 606/79 |
| 5,935,131 A | * | 8/1999 | Bonutti .................. 606/80 |
| 5,964,783 A | * | 10/1999 | Grafton et al. ............ 606/232 |
| 5,976,127 A | * | 11/1999 | Lax ...................... 606/32 |
| 5,993,451 A | | 11/1999 | Burkhart ................. 606/73 |
| 6,013,083 A | | 1/2000 | Bennett .................. 606/104 |

FOREIGN PATENT DOCUMENTS

| | | |
|---|---|---|
| EP | 0 714 666 A1 | 6/1996 |
| WO | WO 97/10743 | 3/1997 |
| WO | WO 97/36555 | 10/1997 |
| WO | WO 98/26814 | 6/1998 |

* cited by examiner

Primary Examiner—Ralph A. Lewis
(74) Attorney, Agent, or Firm—Fish & Richardson P.C.

(57) ABSTRACT

Surgical instruments and methods are provided. In one aspect, a method of securing a fixation device within an opening in a tissue is provided, including delivering a material in a flowable state to said opening, and changing the state of the material so that the material forms an interference fit that secures the fixation device in the opening.

102 Claims, 34 Drawing Sheets

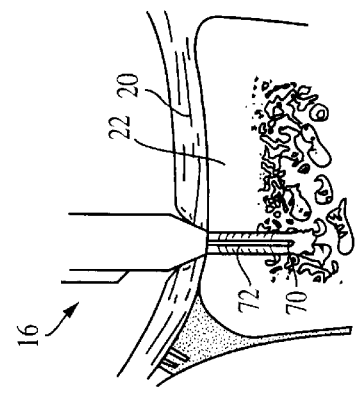
FIG. 2A
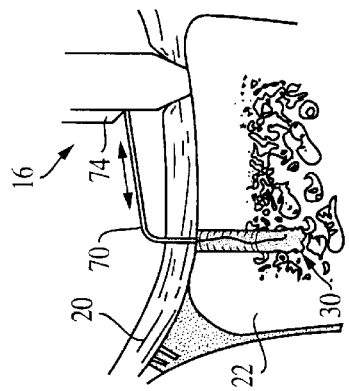
FIG. 2B
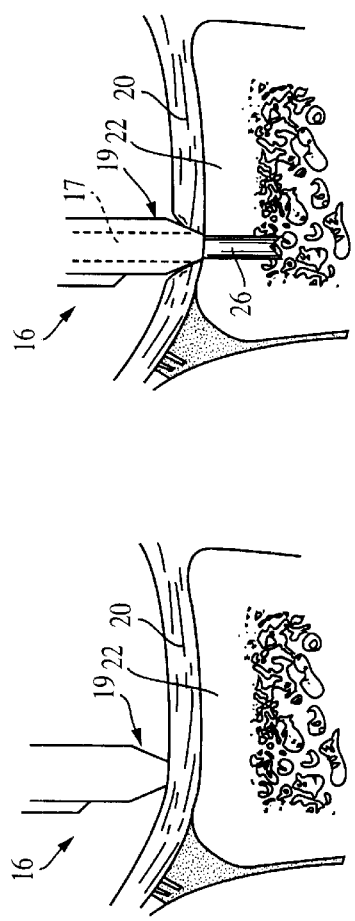
FIG. 2
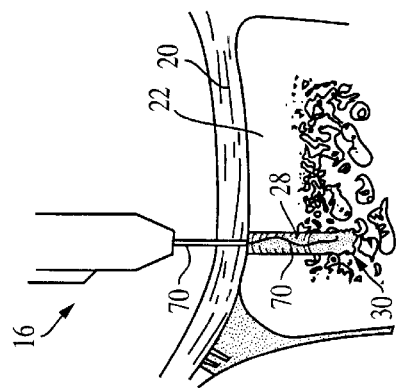
FIG. 2D
FIG. 2E
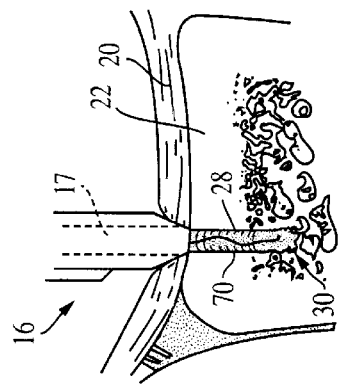
FIG. 2C

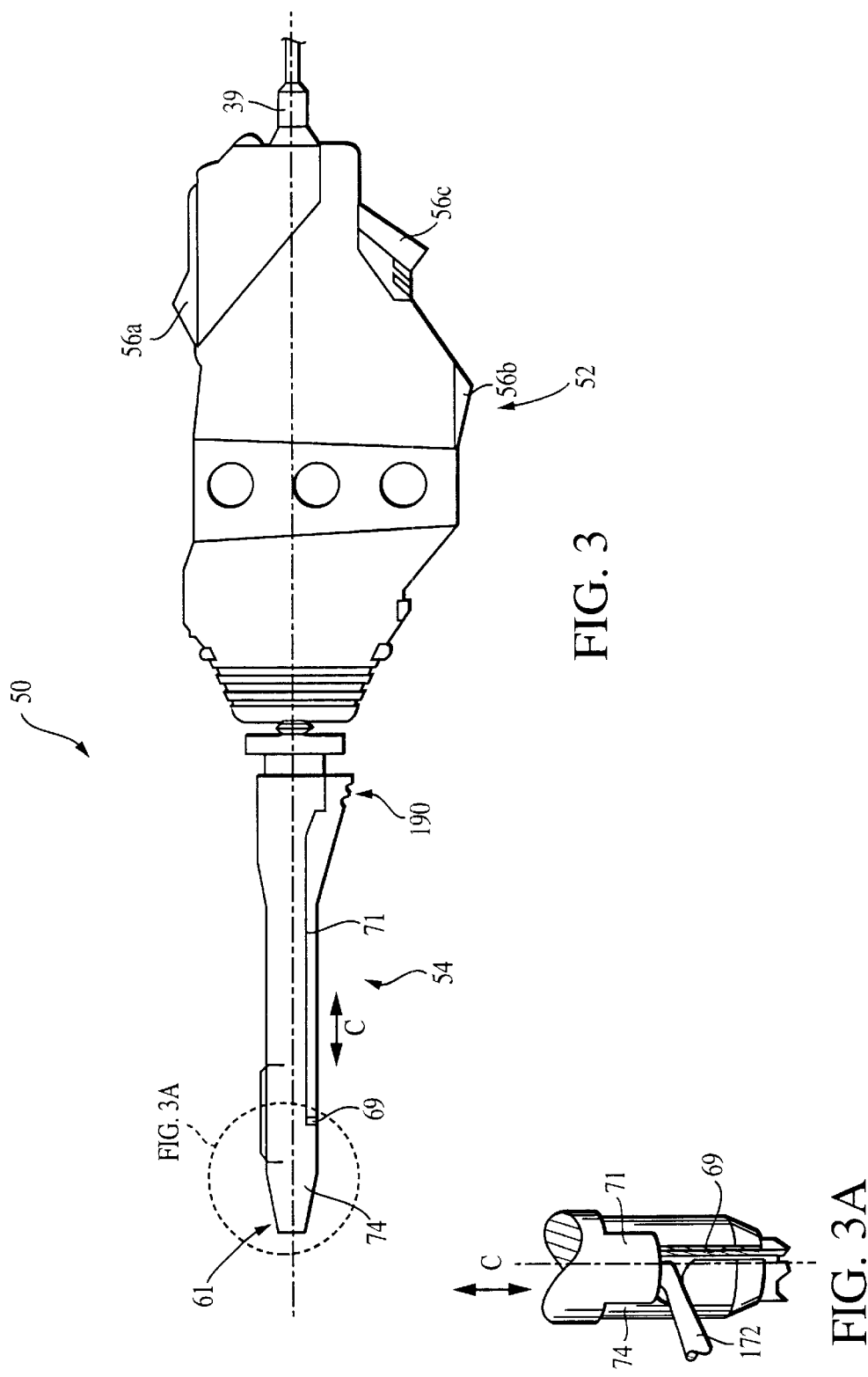

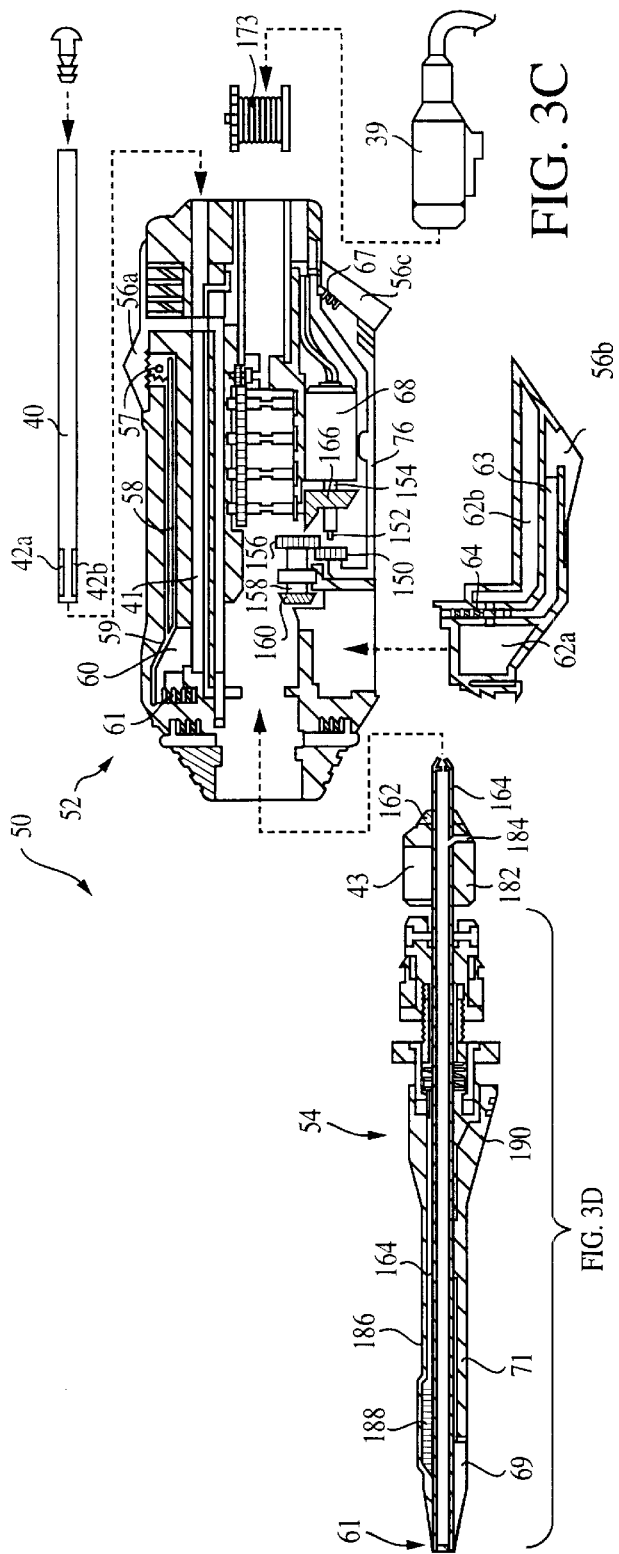
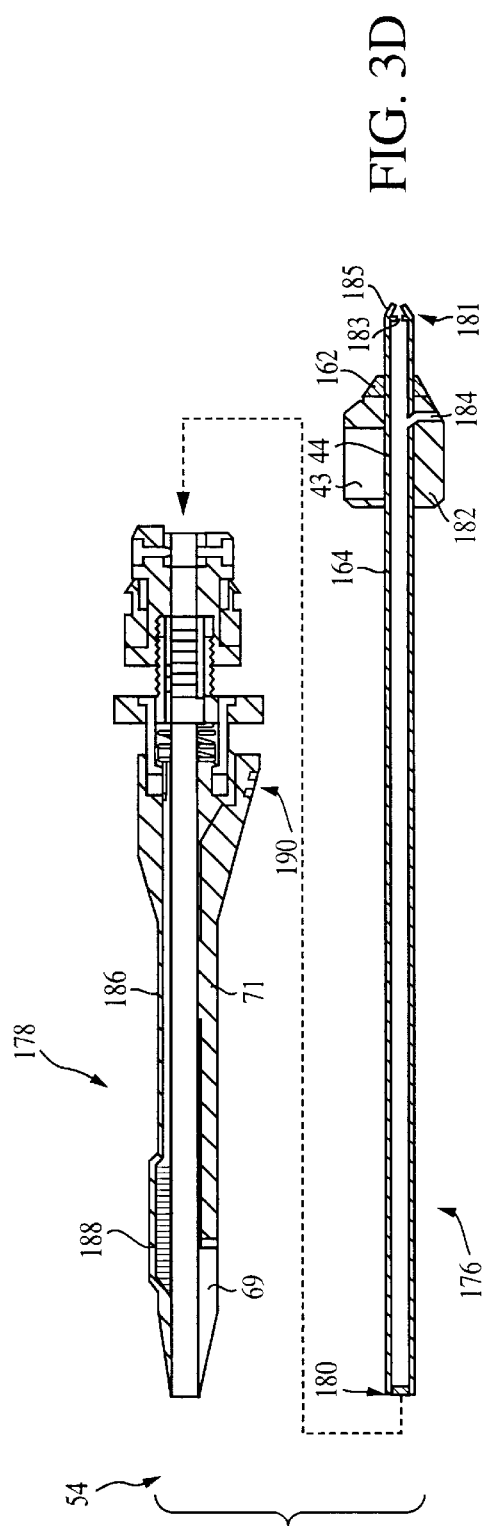
FIG. 3C
FIG. 3D

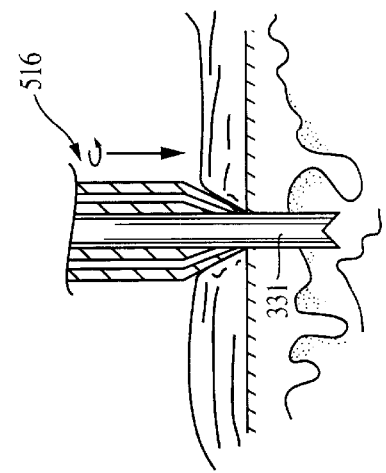
FIG. 12
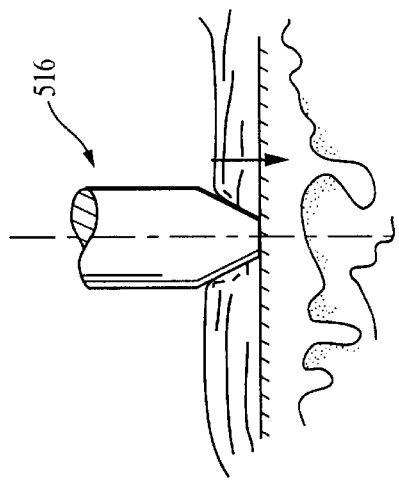
FIG. 12A
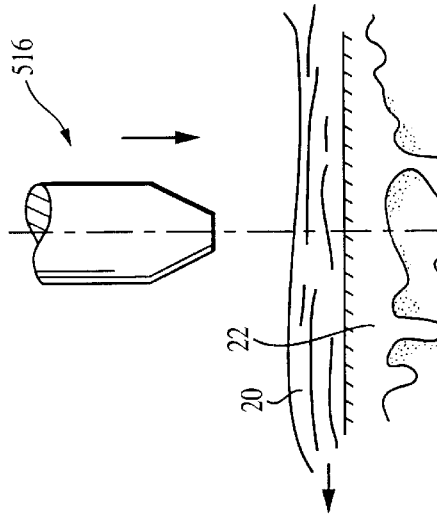
FIG. 12C
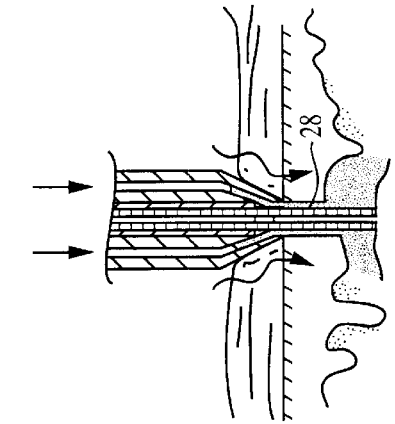
FIG. 12B
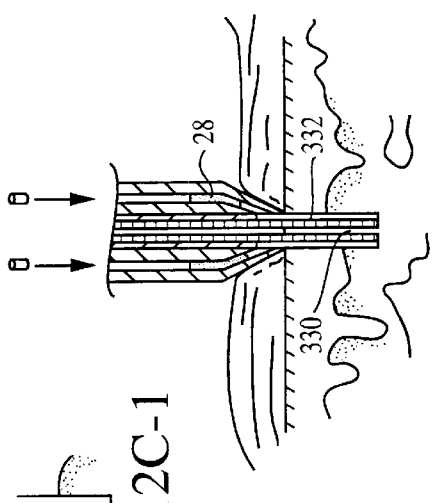
FIG. 12D
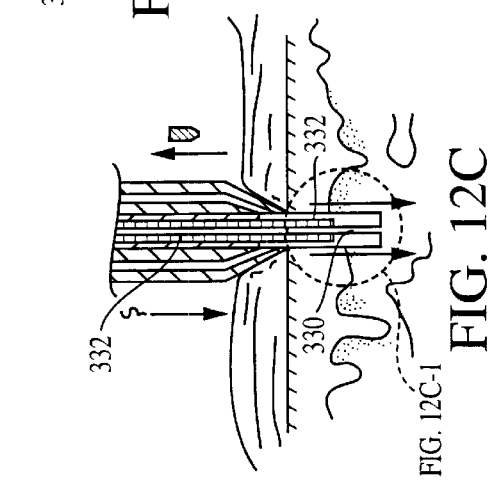
FIG. 12E
FIG. 12C-1

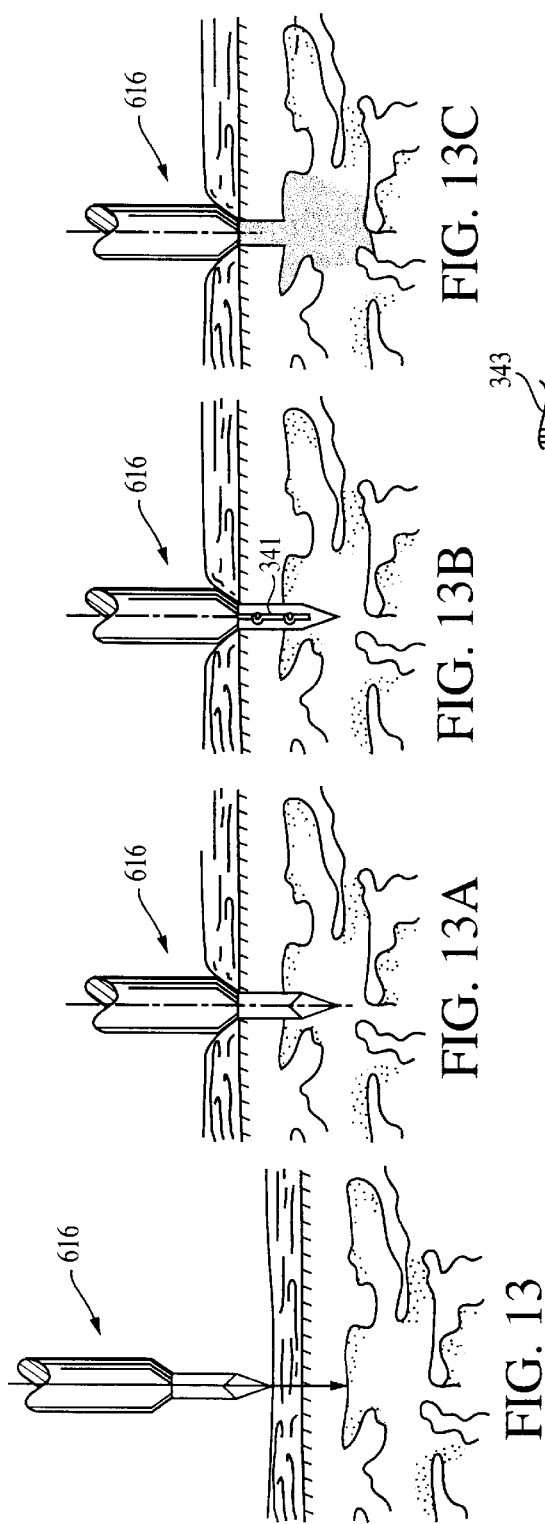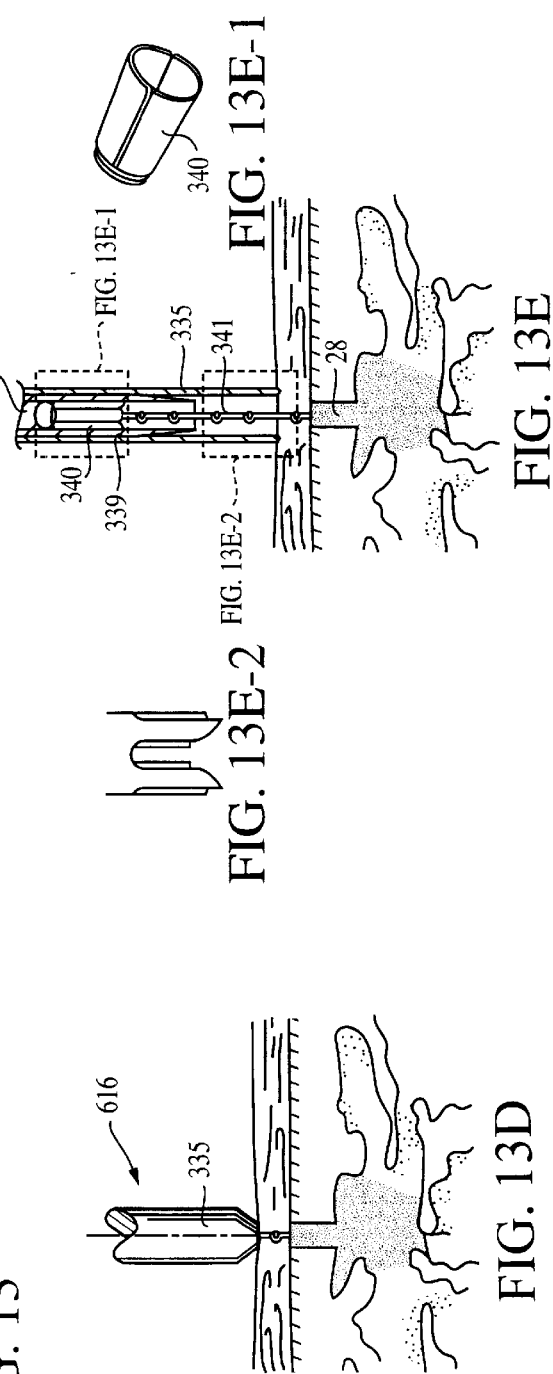

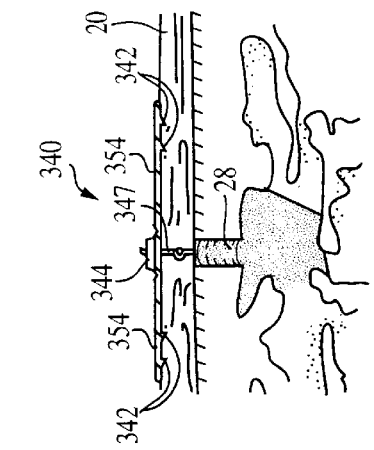
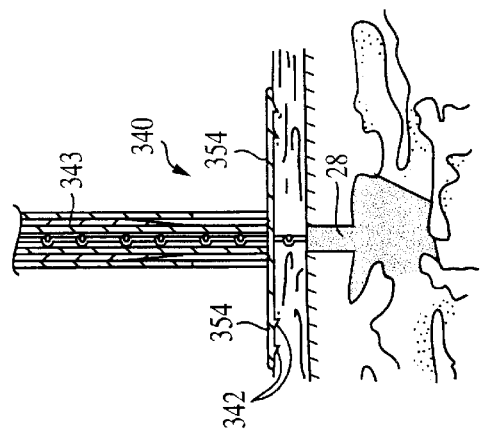
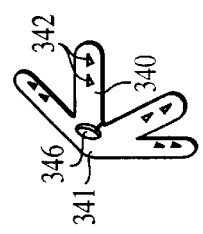
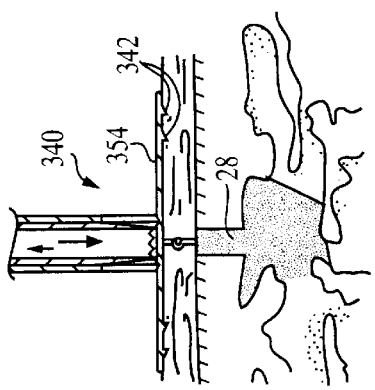
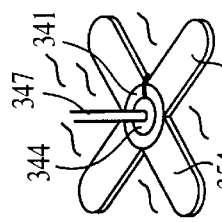
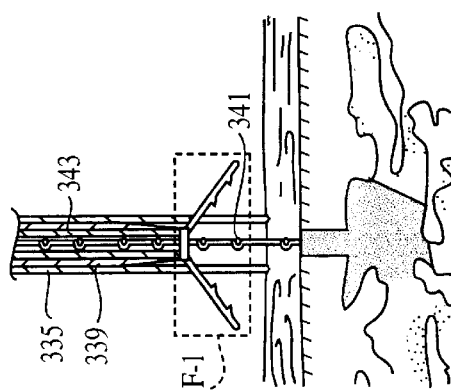
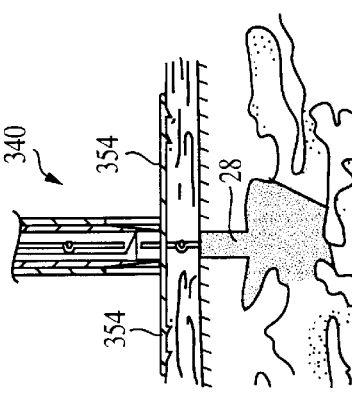

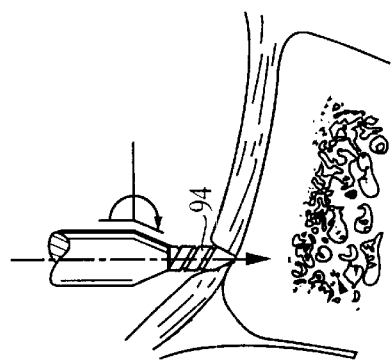
FIG. 14-1
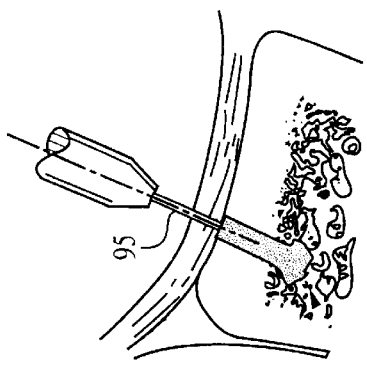
FIG. 14A
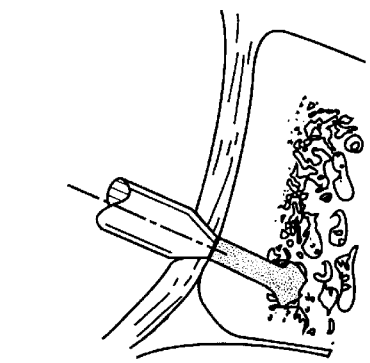
FIG. 14D
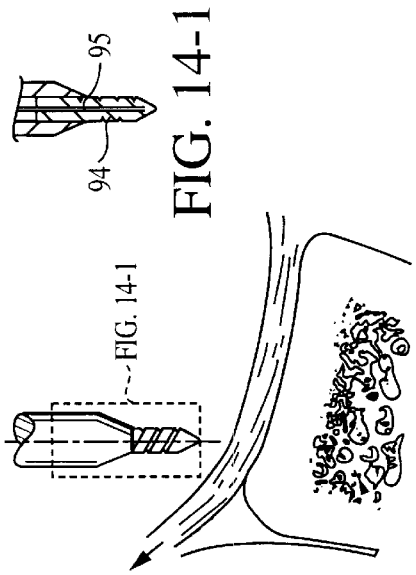
FIG. 14
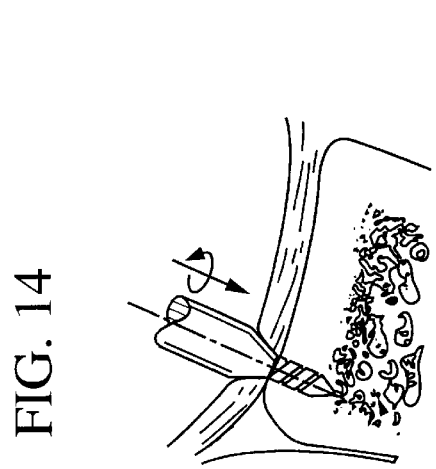
FIG. 14B
FIG. 14C

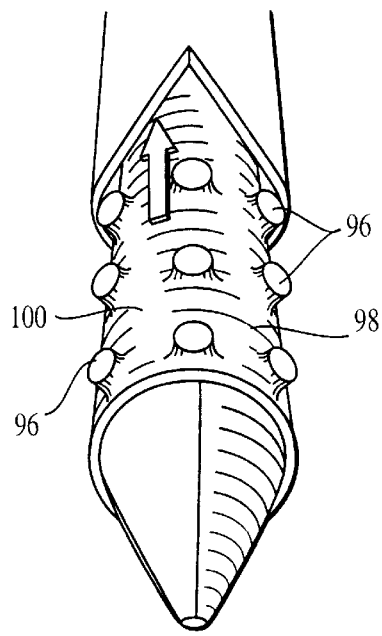
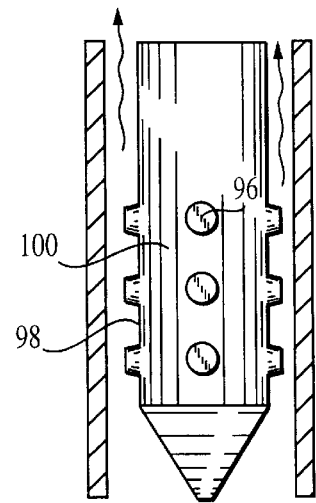
FIG. 15      FIG. 15A
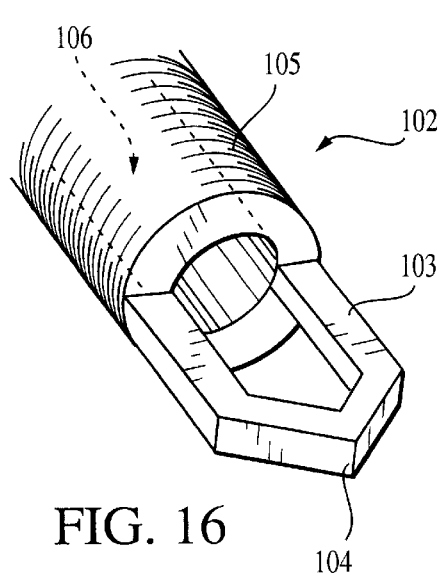
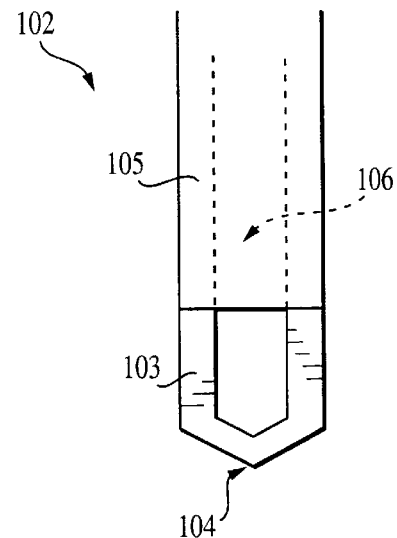
FIG. 16      FIG. 16A

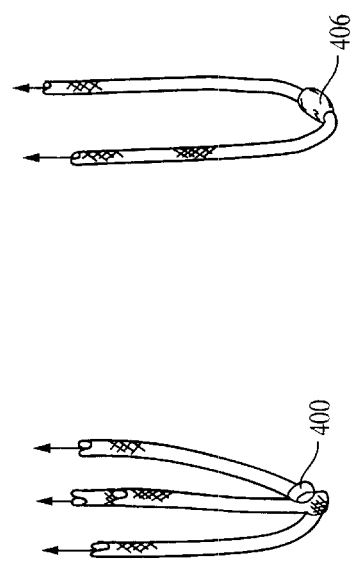
FIG. 21
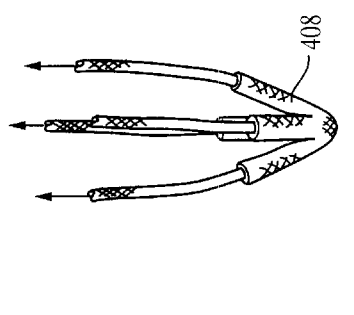
FIG. 21A
FIG. 21B
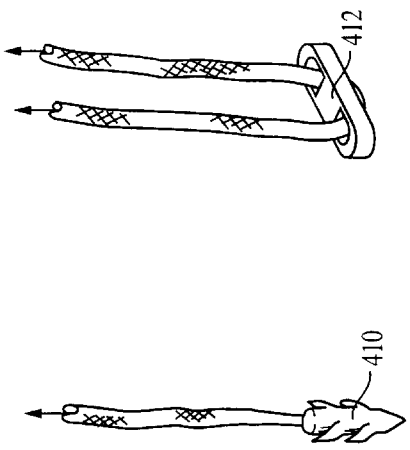
FIG. 21C
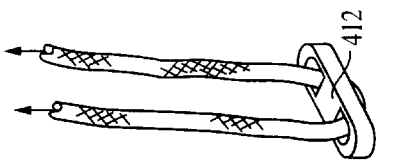
FIG. 21D
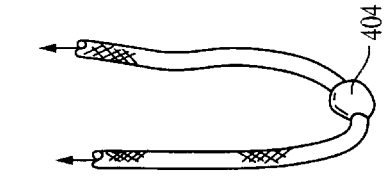
FIG. 21E
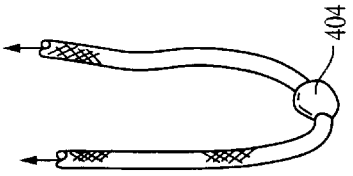
FIG. 21F
FIG. 21G

SURGICAL PROCEDURES AND INSTRUMENTS

TECHNICAL FIELD

This invention relates to surgical procedures and instruments.

BACKGROUND

Many surgical procedures involve fixing soft tissue to bone, particularly in the area of shoulder surgery, for example rotator cuff repairs and instability repair. Generally, in these procedures, the surgeon forms an incision to access the surgical site and then uses one of the following techniques to reattach the soft tissue.

In one technique, the surgeon drills bone tunnels through which a suture is passed. The suture is tied through the soft tissue, which is then reapproximated back to the bone.

In an alternative technique, the surgeon drills a cavity in the bone and inserts a bone anchor. Typically, the bone anchor is formed of metal, plastic or a resorbable material, and is held in place by wings or barbs that deploy outward, by threads or by radial expansion. The anchor includes an eyelet through which a suture is threaded. After placing the anchor, the surgeon ties the suture through the soft tissue, connecting it to the eyelet of the bone anchor and thus reapproximating the soft tissue to the bone.

If multiple sutures are needed to attach the soft tissue, either technique is repeated multiple times at different locations in the bone, with a separate knot tied at each location. It is generally not possible to connect a series of anchors formed using the techniques described above, due to the difficulty of tightening stitches between the anchors.

SUMMARY

According to one aspect of the invention, fixation of soft tissue to bone or to other soft tissue is performed using a flowable material, e.g., a polymer, in place of, or in addition to, a conventional bone anchor. Because the flowable material generally infiltrates the porous cancelous bone (also known as the "trabecular network"), the flowable material effectively forms an anchor that extends under the stronger cortical bone. As a result, an anchor formed in this manner typically exhibits a high pull-out strength. In preferred implementations, bone fragments are incorporated into the flowable material as an autologous filler, to enhance regrowth of bone into the material during natural healing.

Using preferred surgical procedures and instruments of the invention, fixation can be performed endoscopically, rather than in an open surgical procedure, resulting in less invasive treatment with minimal trauma to the patient. In preferred implementations piercing of soft tissue, drilling of a cavity, delivery of a suture and/or bone anchor (if used), and injection of the flowable material into the cavity are performed using a single endoscopic surgical instrument. In some preferred implementations knot-tying, which tends to require considerable skill and dexterity and is generally time-consuming, is not necessary. Thus, the surgical procedures of the invention are generally relatively quick, reducing trauma, and relatively easy to perform. In some implementations, the methods of the invention allow a series of connected, tensioned stitches to be made to fix a region of soft tissue to bone.

In implementations in which a conventional bone anchor is not used with the flowable material, certain risks that may be associated with such bone anchors are eliminated. For example, if a suture is used the suture does not run through an eyelet, and thus will not be microscopically damaged by friction between the suture and eyelet. Also, anchors formed using a flowable material do not rely heavily on the quality and density of the bone in which the anchor is placed, and thus a placement in compromised, low density bone may still exhibit good holding power.

The invention also features surgical procedures involving endoscopic application of polymers for other purposes, e.g., to repair a bone defect, to fill holes that are left when bone plugs are harvested, to repair osteochondritis dessicans injuries, for repair or revision of ACL grafts that exhibit micromovement, for spine fusion, for meniscal repair, and to repair bone fractures. The use of endoscopic devices and techniques significantly reduces invasiveness, generally resulting in less trauma and quicker recovery.

In one aspect, the invention features a method of securing a fixation device within an opening in a tissue, including (a) delivering a material in a flowable state to the opening, and (b) changing the state of the material so that the material forms an interference fit that secures the fixation device in the opening. The fixation device may also be secured in the opening by other, supplemental means, e.g., threaded engagement, but at least a portion of the securing is provided by the interference fit.

Implementations of this aspect of the invention may include one or more of the following features. The tissue includes bone and/or soft tissue. The fixation device is selected from the group consisting of suture, anchors, and screws. The changing step includes allowing the material to at least partially harden. The changing step includes at least partially cross-linking the material. The material includes a polymer, e.g., a thermoplastic polymer. The material includes a hydrogel. The method further includes using the fixation device to secure a second tissue to the tissue having the opening. The tissue having the opening includes bone and the second tissue includes soft tissue. The method further includes, prior to delivery of the material, piercing the soft tissue; forming the opening in an underlying area of the bone; and delivering the fixation device through the pierced tissue; wherein the fixation device is constructed to hold the soft tissue in place against the bone. The fixation device includes a suture. The suture includes a region of increased surface area to enhance anchoring, e.g., a knot, barb, braided area, ball or shaped element. All of the steps of the method are performed endoscopically, for example the steps are performed using a single endoscopic surgical tool having a plurality of attachments, and the tool is not removed from the patient until after the steps are completed. The method further includes incorporating bone fragments, e.g., fragments generated during the forming step, into the material during or prior to the delivering step. The method further includes causing the material to infiltrate the trabecular network. The material includes an osteoconductive filler. The opening is formed using micro-tooling. The opening has a diameter of less than about 3 mm. The forming step includes forming the opening using a consumable cutting tool, and the delivering step includes causing the cutting tool to melt in response to frictional heat generated during the forming step. The forming step includes forming the opening with a cutting tool having a detachable portion, and the method further includes detaching the detachable portion in the opening after the forming step is completed, to serve as the fixation device.

In another aspect, the invention features a method of anchoring soft tissue to bone including (a) piercing the soft tissue; (b) forming an opening in an underlying area of the bone; (c) delivering a material, in a flowable state, to the opening; and (d) molding a portion of the material that is not in the opening to form a fixation device constructed to hold the soft tissue in place against the bone after the material changes state to a relatively less flowable state.

Implementations of this aspect of the invention may include one or more of the following features. The molding step includes forming a portion of the material into a shape that extends radially over a portion of the soft tissue surrounding the opening. The forming step includes drilling or abrading. All of the steps are performed endoscopically. The method further includes incorporating bone fragments generated during the forming step into the material during or prior to the delivering step. The material includes an osteoconductive filler. The method further includes causing the material to infiltrate the trabecular network The opening has a diameter of less than about 3 mm, more preferably from about 0.1 to 6.0 mm. The forming step is performed using micro-tooling. The material includes a polymer. The formed portion extending radially over the soft tissue is coextensive with the material in the opening, defining a bolt-like anchor.

In a further aspect, the invention features a method of fixing soft tissue to bone including (a) at a first location, piercing through the soft tissue; (b) forming an opening in the bone underlying the soft tissue; (c) delivering a fixation device through the pierced tissue to the opening; (d) delivering a material, in a flowable state, to the opening; and (e) causing the material to change state, to a relatively less flowable state, to anchor at least a portion of the fixation device in the opening. The fixation device is selected from the group consisting of suture, anchors and screws. The method further includes (f) drawing the suture across the soft tissue to a second location, and (g) repeating steps (a)–(e) at the second location to form a stitch with the suture between the first and second locations, the stitch securing the soft tissue to the bone. The method further includes gripping the soft tissue to hold it in place against the bone. The method further includes (h) cutting the suture. Steps (a) and (h) are performed with a single tool. Steps (a)–(d) are performed endoscopically. The method further includes repeating steps (f)–(g) at subsequent locations to form a line of connected stitches. Steps (c) and (d) are performed substantially simultaneously, or, alternatively, step (c) is performed prior to step (d). The method further includes delivering the suture as a continuous length from a supply of suture material. The material is provided in the form of a pellet, powder, chips, flakes or rod, and the method further includes melting the material prior to delivery. The method further includes incorporating bone fragments generated during the forming step into the material during or prior to the delivering step. The method further includes incorporating an osteoconductive filler into the material. The method further includes causing the material, in its flowable state, to infiltrate the trabecular network The forming step includes forming a opening having a diameter of less than about 3 mm. The opening has a diameter of from about 0.1 to 6.0 mm. The forming step includes drilling or abrading. The forming step is performed using micro-tooling. The forming step is performed in the bone of a human shoulder.

In yet another aspect, the invention features a surgical instrument for tissue fixation including (a) a handpiece constructed to be held by a surgeon during a fixation procedure; and (b) a fixation instrument, mounted on the handpiece and including (i) a piercing element constructed to pierce through the tissue and form an opening therein; and (ii) a lumen for delivery of a material, in a flowable state, and a fixation device to the opening.

Implementations of this aspect of the invention may include one or more of the following features. The fixation device includes a suture. The surgical instrument further includes a suture feed mechanism constructed to deliver the suture through the lumen to the opening. The surgical instrument is constructed for endoscopic use. The surgical instrument further includes a heating element for heating the material to a molten state. The heating element is mounted on the fixation instrument. The suture feed mechanism includes a movable needle. The surgical instrument further includes a probe constructed to tighten a stitch formed with the suture, e.g., mounted on an external surface of the fixation instrument. The probe is constructed to be manually actuated by a surgeon during an endoscopic procedure. The handpiece includes a reservoir for receiving the material in solid form. The reservoir is constructed to receive a supply of pellets of the material and the handpiece further comprises a mechanism for delivering the pellets from the reservoir to the lumen. Alternatively, the reservoir is constructed to receive a supply of powdered material and the handpiece further comprises a mechanism for delivering a predetermined dose of powdered material from the reservoir to the lumen. The fixation instrument is detachable from the handpiece. The surgical instrument further includes a mixing device constructed to mix bone fragments and debris generated during opening forming into the material prior to delivery to the opening. The surgical element further includes a drive mechanism constructed to drive the piercing element and, if it is included, the suture feed mechanism. The drive mechanism is disposed in the handpiece. The surgical instrument further includes a clutch mechanism constructed to allow a surgeon to selectively engage and disengage the drive of the piercing element and the drive of the suture feed mechanism. The handpiece is constructed to receive attachments other than the fixation instrument. The piercing element is constructed to cut the suture. The fixation instrument is constructed to perform a complete fixation procedure without removing the fixation instrument from the surgical site.

In another aspect, the invention features a surgical method including (a) forming an opening in bone of a patient; (b) incorporating bone fragments generated during the forming step into a polymer as an autologous filler to form a bone/polymer blend; and (c) delivering the bone/polymer blend, in a flowable state, to the patient; wherein steps (a)–(c) are performed endoscopically. In some implementations, the bone/polymer blend is delivered to the opening.

In yet another aspect, the invention features a method of securing a first layer of soft tissue to a second layer of soft tissue including (a) forming an opening extending through both layers of soft tissue; (b) delivering a material, in a flowable state, through the opening so that the flowable material extends beyond the soft tissue at each end of the opening; and (c) causing the material to change state, to a relatively less flowable state, forming an anchor to secure the two layers of soft tissue together.

In a further aspect, the invention features a method of securing a first layer of soft tissue to a second layer of soft tissue including (a) forming an opening extending through both layers of soft tissue; (b) delivering a thermoplastic member to the opening, so that a portion of the member extends beyond the soft tissue at each end of the opening; (c) softening the extending portions of the member; and (d) forming each of the softened extending portions so that each extends radially over a portion of the soft tissue to secure the two layers of soft tissue together.

In some implementations, the member includes a hollow tube and the forming step results in a rivet-like anchor.

In another aspect, the invention features a method of securing two tissues together including (a) forming an opening extending through the two tissues, (b) delivering a material, in a flowable state, to the opening, and (c) causing the material to change state, to a relatively less flowable state; wherein the material forms an anchor that secures the two tissues together. In some implementations, the anchor is a bolt-like anchor.

In a further aspect, the invention features an endoscopic instrument for securing two tissues together including (a) a piercing device constructed to form an opening extending through the two tissues; and (b) a delivery device constructed to deliver a material, in a flowable state, and a fixation device, to the opening.

In another aspect, the invention features surgical instruments constructed to perform the steps of the methods described above. Preferred instruments are constructed to perform all steps of the methods endoscopically.

Other features and advantages of the invention will be apparent from the description and drawings, and from the claims.

DESCRIPTION OF DRAWINGS

FIGS. 3–3E are views of a surgical instrument suitable for performing the method shown in FIGS. 2–2K. FIG. 3 is a side view of the surgical instrument. FIG. 3A is a highly enlarged detail perspective view of area A of FIG. 3. FIG. 3C is an exploded cross-sectional view of the surgical instrument of FIG. 3. FIG. 3D is an exploded view of area D of FIG. 3C. FIG. 3E is an exploded view showing an enlarged cross-sectional view of the polymer cartridge of the instrument.

FIGS. 13–13J are diagrammatic views of yet another alternative procedure for fixing soft tissue to bone.

FIGS. 14–14D are diagrammatic views showing a cavity being drilled with a consumable drill bit.

FIGS. 15 and 15A are perspective and side views, respectively, of an alternative cutting tool.

FIGS. 16 and 16A are perspective and side views, respectively, of an alternative cutting tool.

FIGS. 21–21G are diagrammatic views of various types of augmented sutures.

DETAILED DESCRIPTION

Figure 1:
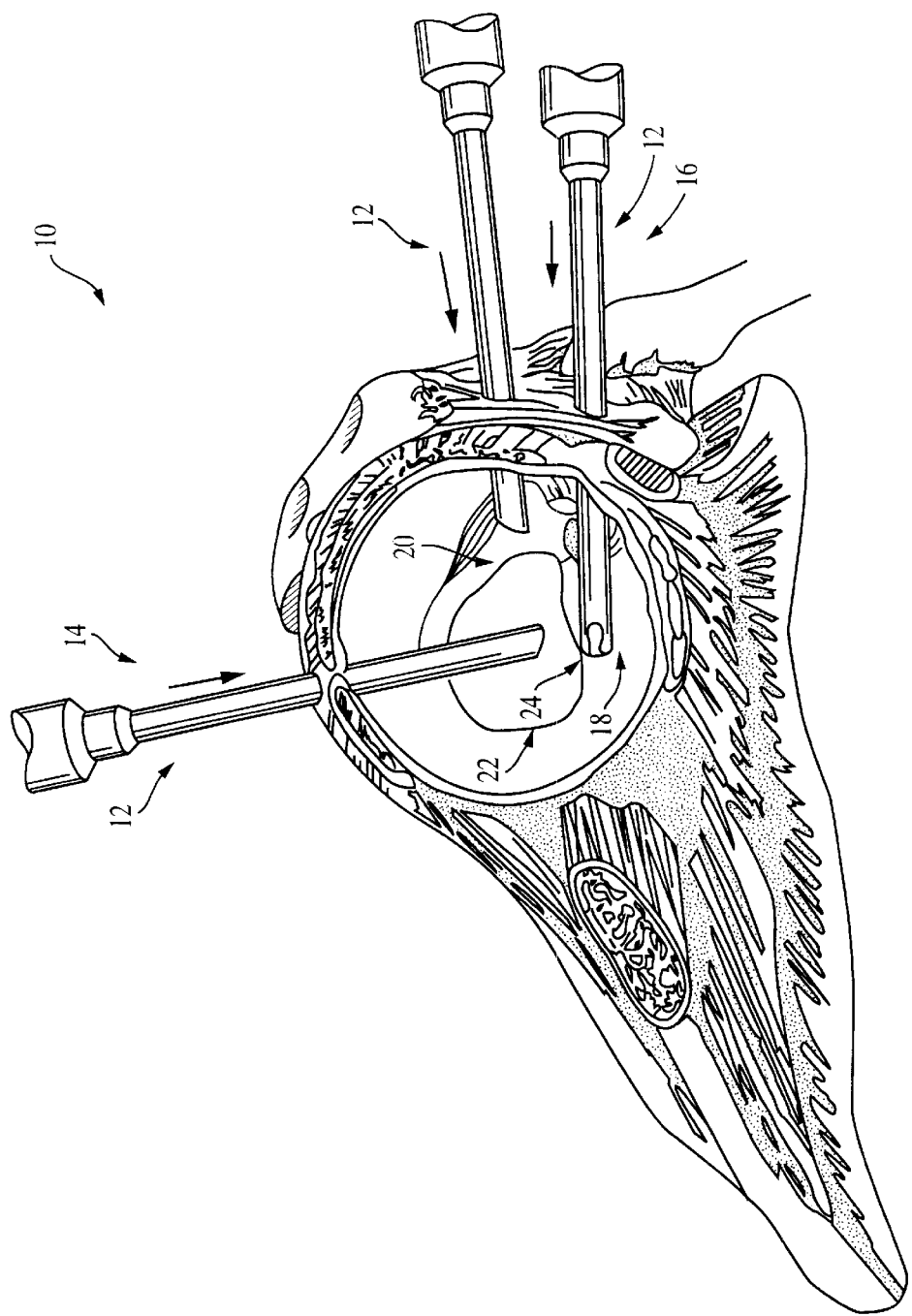
FIG. 1 is a diagrammatic perspective view of the surgical environment of an endoscopic procedure according to one embodiment of the invention.

Referring to FIG. 1, a surgical site 10 includes a number of portals 12, through which endoscopic devices can be inserted. The surgeon can view the surgical site using an arthroscope 14, while placing a polymeric anchor, as will be discussed in detail below, using a surgical instrument 16. Surgical instrument 16 generally depicts an instrument for placing a polymeric anchor. Examples of particular instruments that are suitable for use in the various methods of the invention will be discussed in further detail below. In the initial step shown in FIG. 1, the surgeon is using a shaver 18 to remove a portion of soft tissue 20, expose the surface 24 of bone 22 and create a bleeding bone bed, in preparation for the surgical procedures described below. While shaver 18 is shown as a separate instrument in FIG. 1, it may instead be integrated with surgical instrument 16.

Figure 2F:
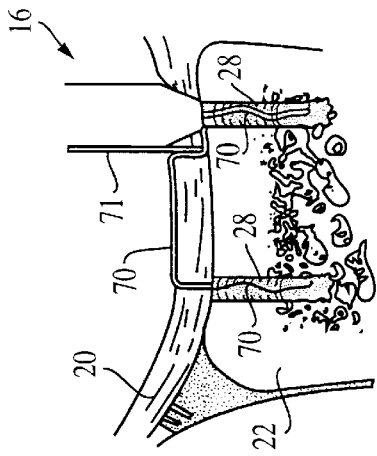
FIGS. 2–2K are diagrammatic views of a procedure for forming a series of polymeric anchors connected by stitching.
Figure 2G:
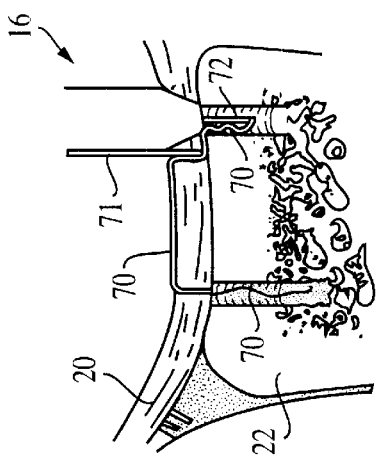
Figure 2H:
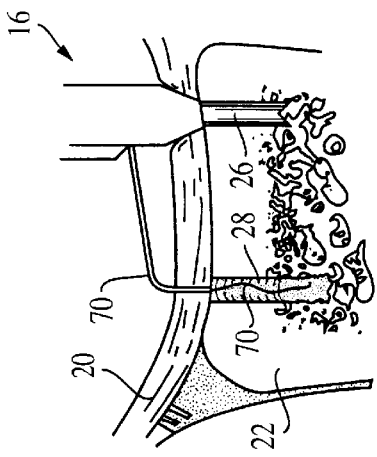
Figure 2J:
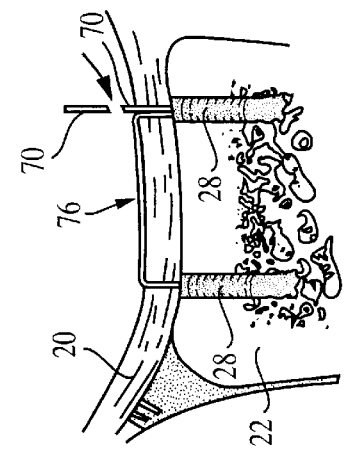
Figure 2I:
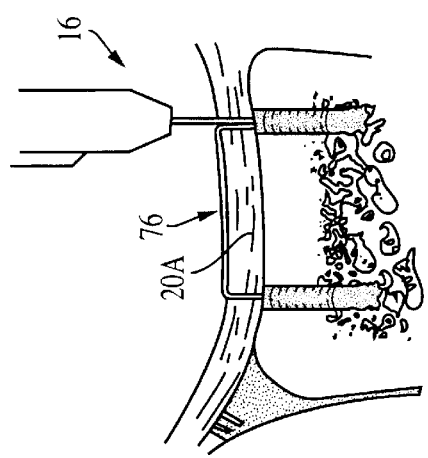
Figure 2K:
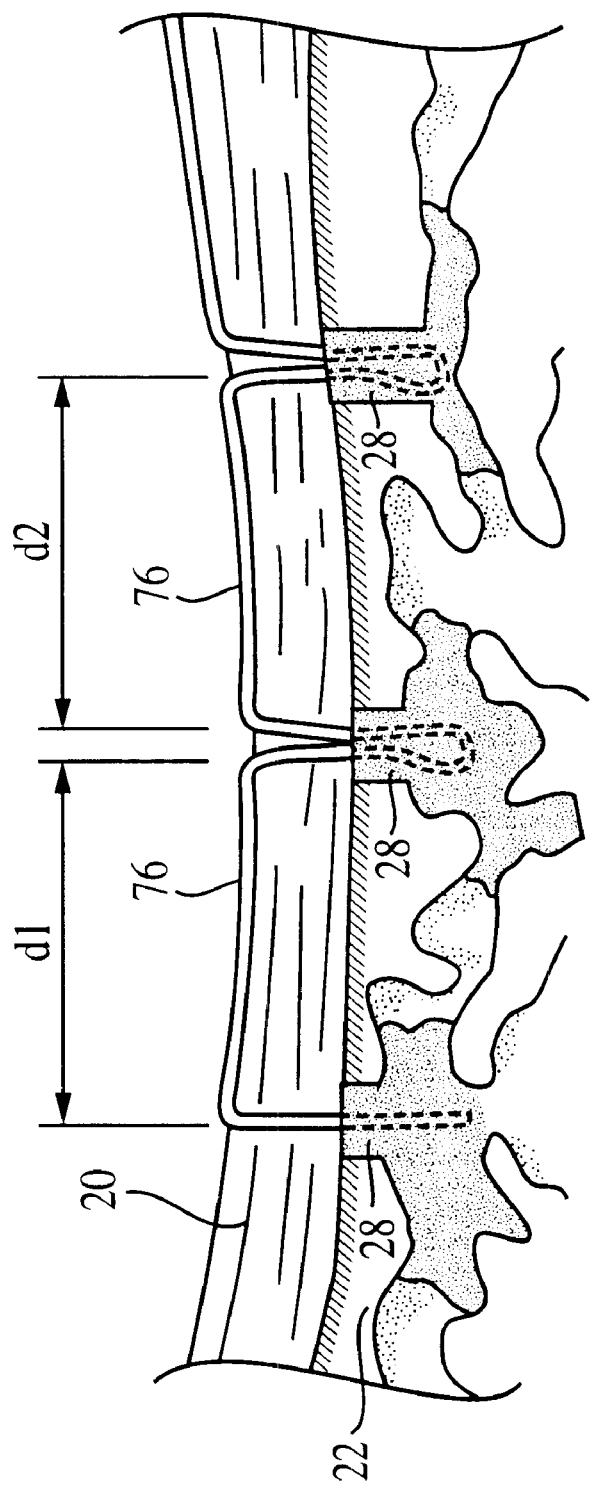

A procedure for fixing soft tissue to bone is shown in FIGS. 2–2K. In this procedure, one or more stitches are formed to fix the soft tissue to the bone over an area. The steps shown in FIGS. 2–2K are performed endoscopically, in the environment shown in FIG. 1. However, for the sake of clarity, only the surgical instrument 16, the bone and the soft tissue are shown in FIGS. 2–2K.

The steps shown in FIGS. 2–2K are performed using an endoscopic surgical instrument 16 that is constructed to perform a stitching operation. Generally, surgical instrument 16 includes a cannulated tube, a cutting tool within the cannulated tube, and a drive mechanism constructed to power the cutting tool to pierce soft tissue and form a cavity in the underlying bone. The drive mechanism is programmable, to allow the cutting tool to be either rotated or reciprocally oscillated (i.e., rotated back and forth through successive cycles, each rotation cycle being less than 360 degrees), as desired, for reasons that will be discussed below. The surgical instrument also includes a supply of suture material, e.g., on a spool, a mechanism for advancing the suture material through the cannulated tube, a chamber containing a supply of polymer in solid form (e.g., powder or pellets), and a heating element for melting the polymer for delivery in molten form. When the cutting tool is retracted, the suture and polymer are delivered through the cannulated tube, as will be described below, to anchor a portion of the suture in the cavity. Optionally, the surgical device may include a cannulated needle for positioning the suture in the cavity.

Using surgical instrument 16, a stitching procedure is performed as follows. First, the soft tissue 20 is held in place by the proximal end 19 of surgical instrument 16, and pierced by a cutting tool 26 (FIG. 2A). Cutting tool 26 also forms a cavity in bone 22 (FIG. 2A). Next, the cutting tool is retracted and a suture 70 is fed through the cannula 17 of the surgical instrument 16, e.g., from a reel of suture material (not shown) in the surgical instrument. The suture 70 may be positioned in the cavity by advancing a cannulated needle 72, through the cannula of which the suture is fed, into the cavity, as shown in FIG. 2B. Alternatively, the suture may be positioned by gravity or in any suitable manner.

After the suture is positioned, needle 72 is retracted and molten polymer 28 is injected into the cavity around suture 70 (FIG. 2C). The polymer 28 penetrates through the side walls and bottom of the cavity into the trabecular network (cancelous bone) in region 30.

Once polymer 28 has at least partially solidified, anchoring the suture in the cavity, the surgical instrument 16 is retracted (FIG. 2D), and suture 70 is fed from the surgical instrument as the surgical instrument is moved to a second location (FIG. 2E). As shown in FIG. 3A, and discussed in further detail below, as the suture 70 is fed from the instrument it exits the instrument through an inverted-L-shaped channel 69 extending up the side 74 of the surgical instrument, so that the suture is not cut during the piercing of the soft tissue.

When the surgical instrument is positioned at the second location, the surgical instrument again holds the soft tissue 20 in place, and cutting tool 26 again pierces the soft tissue 20 (FIG. 2E). The cutting tool 26 is then reciprocally oscillated to form a second cavity, as shown in FIG. 2F. (At this stage, the cutting tool cannot be rotated 360 degrees, as this would cut or break the suture, or cause the suture to wind around the cutting tool. Thus, the surgeon sets the programmable drive mechanism to an oscillating mode. The surgeon can use either a rotating or an oscillating motion to form the first cavity (FIG. 2A), depending on the surgeon's preference.) The suture 70 is fed from the supply reel into the new cavity, and positioned by advancing needle 72 into the cavity, as shown in FIG. 2G (as discussed above, the suture could instead be positioned by gravity).

A probe 71 is used to press the suture through the soft tissue, compressing the soft tissue against the surface of the bone in the vicinity of the second cavity and tensioning the suture material as it passes between the cavities, tightening the "stitch" that will be formed between the cavities. Needle 72 is retracted, leaving a loop of suture material (not shown) in the cavity, and molten polymer 28 is injected into the second cavity around the suture 70 (FIG. 2H).

Once the polymer in the second cavity has at least partially solidified, the surgical instrument 16 is again retracted (FIG. 2I). At this point, a "stitch" 76 of suture extends between the first and second cavities, holding region 20A of the soft tissue 20 securely against bone 22. The stitching procedure can then be terminated, as shown in FIG. 2J, by cutting the suture, or stitching can be continued, by repeating the above steps, to form a line of stitches as shown in FIG. 2K. The stitches can be of uniform lengths, or of different lengths (i.e., d1 may or may not be equal to d2). The suture can be cut, at the end of the procedure, using the surgical instrument 16 or a separate tool, e.g., a scalpel that is inserted through the cannula of an endoscope.

The polymer used in the procedure described above is preferably provided in the form of a plurality of pellets or a powder, and is preloaded into the surgical instrument prior to surgery, as will be described in further detail below. One pellet or shot of powder is used to fill each cavity. The pellets or powder are melted, to form the molten polymer, immediately prior to injection.

Many types of instruments may be suitable for use as surgical instrument 16 in the procedure described above with reference to FIGS. 2–2K. An example of a suitable surgical instrument, stitching instrument 50, is shown in FIGS. 3–3E.

Figure 7:
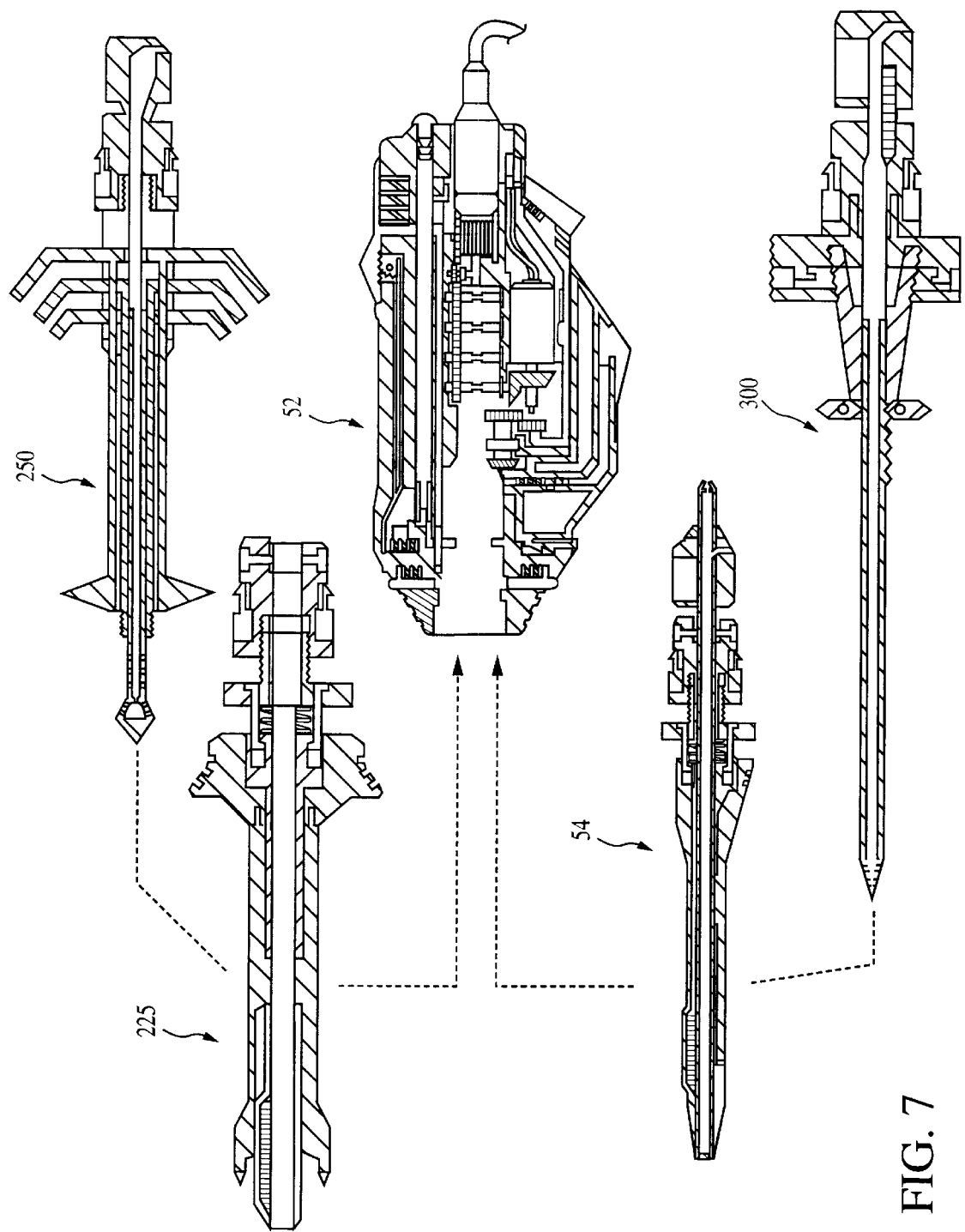
FIG. 7 is a diagrammatic cross-sectional view showing a handpiece and a number of interchangeable attachments that are mountable on the handpiece.

Instrument 50 includes a handpiece 52, and a removable attachment device 54. As indicated in FIG. 7, and discussed further below, attachment device 54 is one of many modular attachment devices that may be interchangeably mounted on handpiece 52. The attachment devices may be disposable. The handpiece 52 is sterilizable and is designed for repeated use, e.g., 100 uses or more. The attachment devices are clipped into the handpiece, on a bearing, as is well known for endoscopic surgical instruments with interchangeable attachments, such as those commercially available from Smith & Nephew, Andover, Mass., under the tradename DYONICS™.

Referring to FIG. 3, handpiece 52 is constructed to be held by a surgeon during a surgical procedure, and includes switches 56a, 56b and 56c that are positioned to be easily actuated by the surgeon to control the functions of the surgical instrument, as will be discussed below. Handpiece 52 is connected to a power supply by an adapter cord 39 (e.g., a Dyonics EP1 power supply cord, available from Smith & Nephew). The handpiece 52 may be fitted with interchangeable molded grips, e.g., two-piece housings that snap on over the handpiece 52 and include recesses through which switches 56 extend, thus providing the surgeon with a more customized grip.

Figure 3B:
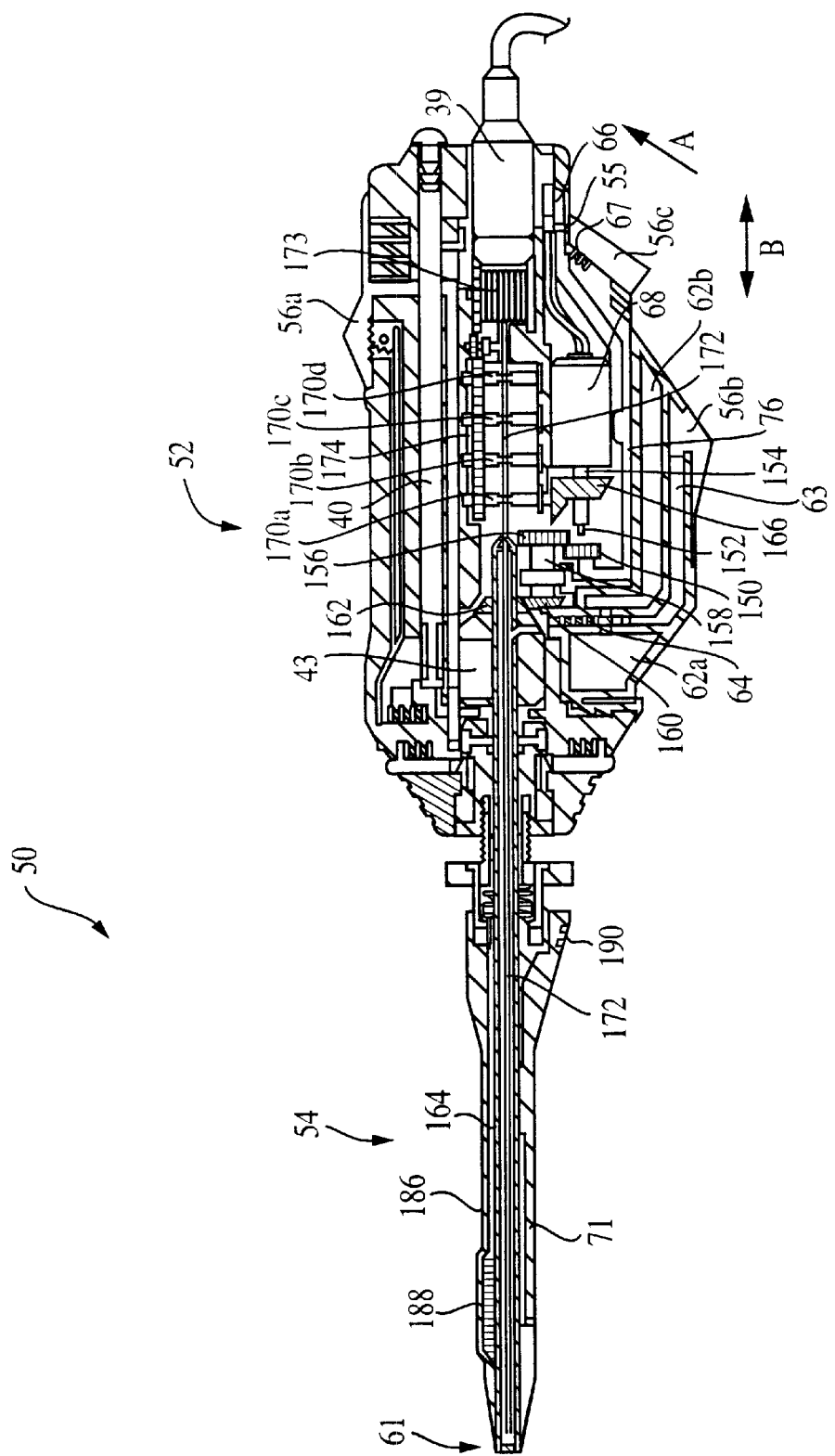
FIG. 3B is a cross-sectional view of the surgical instrument of FIG. 3.
Figure 3E:
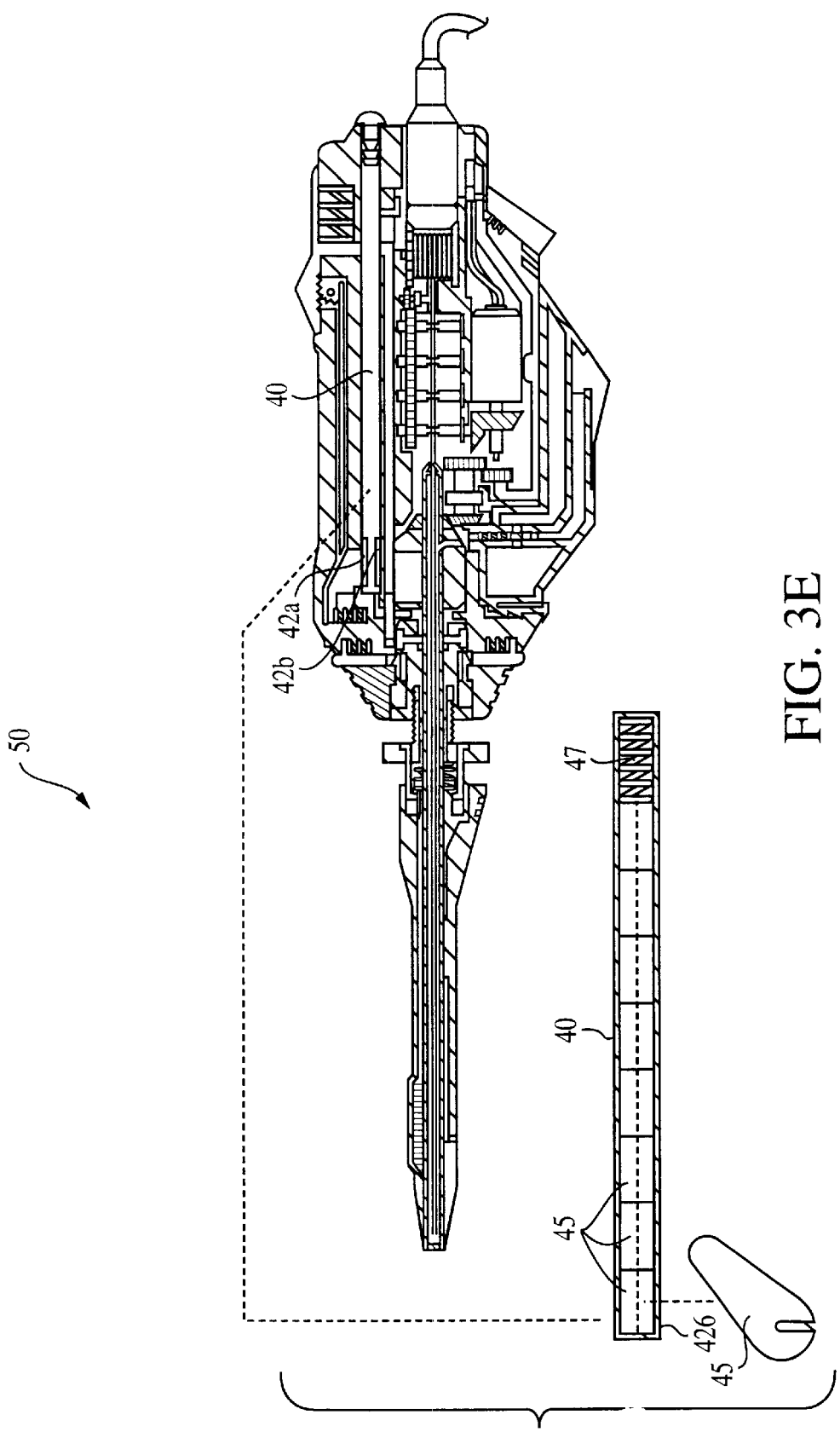

Referring now to FIGS. 3B and 3C, the handpiece 52 includes a removable polymer cartridge 40 that is preloaded with a supply of polymer pellets 45 (FIG. 3E) prior to surgery, and a chamber 41 (FIG. 3C) for receiving the polymer cartridge. The polymer cartridge 40 includes aligned slots 42a, 42b, through which a pellet can be pushed out for delivery to a cavity.

To push a pellet out of the cartridge for delivery, the surgeon pulls back on switch 56a. This causes toothed cam 57 to push rod 58 against inclined surface 59 of block 60, causing block 60 to move downward through slot 42a, thereby displacing the pellet through slot 42b into chamber 43 through an cavity that is not shown in the cross-section of FIG. 3B. The pellet then passes into the lumen of the attachment 54 through an cavity 44 (FIG. 3D). After the pellet has been dispensed, block 60 is returned to, and biased in, its previous position by spring 61. This reverses the movement of the rod 58 and toothed cam 57, returning the switch 56a to its normal position. The pellets are advanced toward the proximal end of the cartridge, to move a new pellet into place for delivery through slot 42b, by spring 47 (FIG. 3E).

The polymer pellet is moved to the delivery end 61 (FIG. 3B) of the instrument 50 by compressed gas delivered from pre-filled reservoirs 62a and 62b. To deliver air to move the pellet, the surgeon pushes switch 56b forward, which moves a hydraulic fluid in chamber 63 against spring 64, cavity a valve (not shown) to release the compressed gas from the reservoirs into the lumen of the attachment 54.

The cutting tool (cutting device 176, discussed below) and the suture delivery mechanism are both driven by a single motor, and a clutch mechanism and switch are provided to allow the surgeon to selectively activate the piercing/cavity forming function of the cutting device and the suture delivery function (performed by the suture delivery mechanism), as will be discussed below. The motor is normally off, and is activated by the surgeon pressing switch 56c upward (arrow A, FIG. 3B), moving contact 65 into engagement with contact 66 of motor 68. The switch is held in the engaged position by a catch (not shown), so that to deactivate the motor the surgeon needs to press the switch upward again, as which point spring 67 will return the switch to its normal position.

The surgeon can select between the piercing/cavity forming function and the suture delivery function by moving switch 56c back and forth axially (arrow B, FIG. 3B). This causes member 76 to move axially, engaging a set of gears that drives one of these functions and disengaging a set of gears that drives the other function, as will be discussed further below.

When the suture delivery function is selected, i.e., when switch 56c is in the position shown in FIG. 3B (its left-hand position), bevel gear 166, mounted on drive shaft 154 of the motor, is engaged with bevel gear 168, which drives a suture feed cog 170a, through which a suture 172 (FIG. 3B) is fed from a reel 173. A series of bearings 174 drive suture feed cogs 170b–170d, which advance the suture towards the delivery end 61 of the surgical instrument.

When the piercing/cavity forming function is selected, i.e., when switch 56c is moved to the right in FIG. 3B, a spline (not shown) in the center of cog 150 engages end 152 of drive shaft 154 of the motor. Simultaneously, the teeth of cog 150 engage the teeth of cog 156, causing shaft 158 to rotate, driving bevel gear 160 which engages bevel gear 162 on the cutting tube 164 of attachment 54. Engagement of bevel gears 160 and 162 rotates the cutting device 176 (or oscillates the cutting device, depending on the setting of the programmable drive). The motor is programmed to stop rotation, when the piercing/cavity forming function is deselected, in a position in which cavity 44 is aligned with the polymer-delivery cavity in the handpiece that is in turn aligned with cavity 42b of the polymer cartridge.

Referring to FIG. 3D, the attachment 54 includes an inner cutting device 176 that slides into an outer guide/heating device 178 when the surgical instrument is assembled for use. When the instrument is assembled, as shown in FIG. 3C, the guide/heating device 178 snaps into the handpiece 52, and the cutting device 176 is trapped between the handpiece 52 and the guide/heating device 174.

Cutting device 176 includes a cannulated cutting tube 164 having a cutting tip 180, a member 182 that defines chamber 43 and a gas inlet 184, and bevel gear 162. End 181 of the cutting tube includes a flap valve 183 to prevent the compressed gas from escaping through end 181. When the suture delivery function is selected, the pressure of the end of the advancing suture opens valve 183, and the suture is guided through the cavity at end 181 by a conical portion 185.

Guide/heating device 174 includes a cannulated guide tube 186 and, within the guide tube, a heating element 188 for melting the polymer pellets. The guide tube 186 includes a movable probe portion 71, which can be moved axially (arrows C, FIGS. 3 and 3A) by the surgeon, using grip 190, to push the suture 172 against the soft tissue as discussed above. The probe portion is in its upper position in FIG. 3A, allowing clearance for the suture as it feeds from the tip. It is lowered prior to dispensing the polymer (to keep the polymer from escaping through channel 69), and to tighten the suture when a stitch is formed. The guide tube 186 is spring loaded so that it will retract under pressure when pressed against the soft tissue, allowing the cutting tip to penetrate the bone to a desired depth which is determined by the degree of spring loading. When pressure is released, the guide tube is biased by the spring load back to its normal, extended position. The guide/heating device also includes an attachment portion 200 that releasably snap fits into the handpiece.

Thus, to use the stitching instrument 50 in the procedure shown in FIGS. 2–2K and described above, a surgeon would first preload a supply of polymer into the instrument 50, by installing polymer cartridge 40, preprogram the programmable drive mechanism as desired, and move probe portion 71 to its lowered position. The surgeon would then press the delivery end 61 of the device against the soft tissue, and select the piercing/cavity forming function by moving switch 56c to the appropriate position, to pierce the soft tissue and form a cavity. Next, the surgeon would move switch 56c to select the suture delivery function, and deliver a desired amount of suture material to the cavity. After delivery of the suture, the surgeon would move switch 56c to deactivate the drive motor (turning off both the piercing/cavity forming and suture delivery functions), and pull back on switch 56a and push forward on switch 56b to deliver polymer to the cavity. Once the polymer had at least partially solidified, the surgeon would raise probe portion 71, move switch 56c to select the suture delivery function, and feed out suture while moving the instrument 50 to a second location. At the second location, the surgeon would move switch 56c to select the piercing/cavity forming function, and form a second cavity. The surgeon would then move switch 56c to select the.suture delivery function, deliver a desired amount of suture to the cavity, move switch 56c to deactivate the drive motor, lower probe portion 71 to tighten the "stitch" between the cavities, and move switches 56a and 56b to deliver polymer to the cavity. These steps would be repeated to form as many stitches as desired.

If desired, the surgical instrument may be used to deliver polymer without performing any cutting procedure.

Figure 4A:
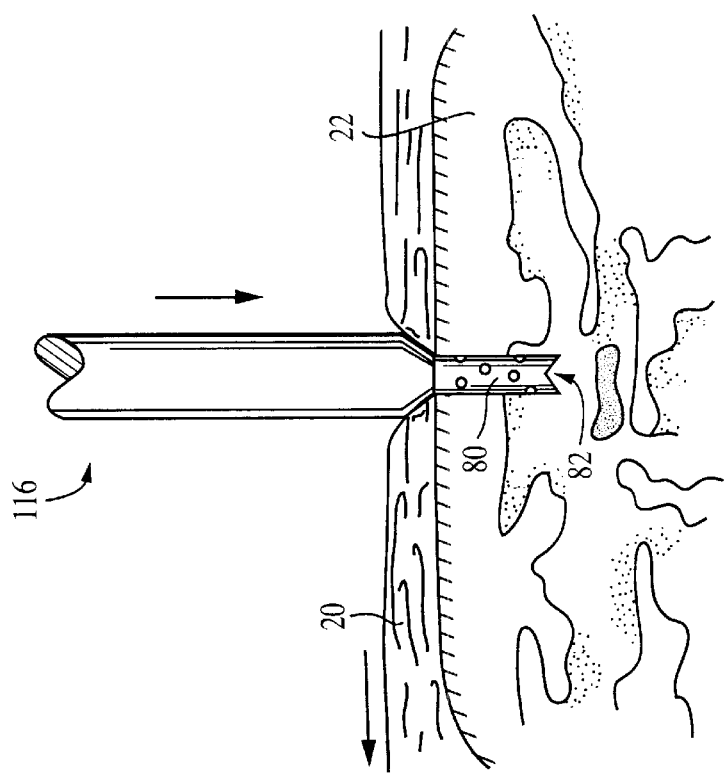
FIGS. 4–4J are diagrammatic views of an alternative procedure for forming a series of polymeric anchors connected by stitching.
Figure 4:
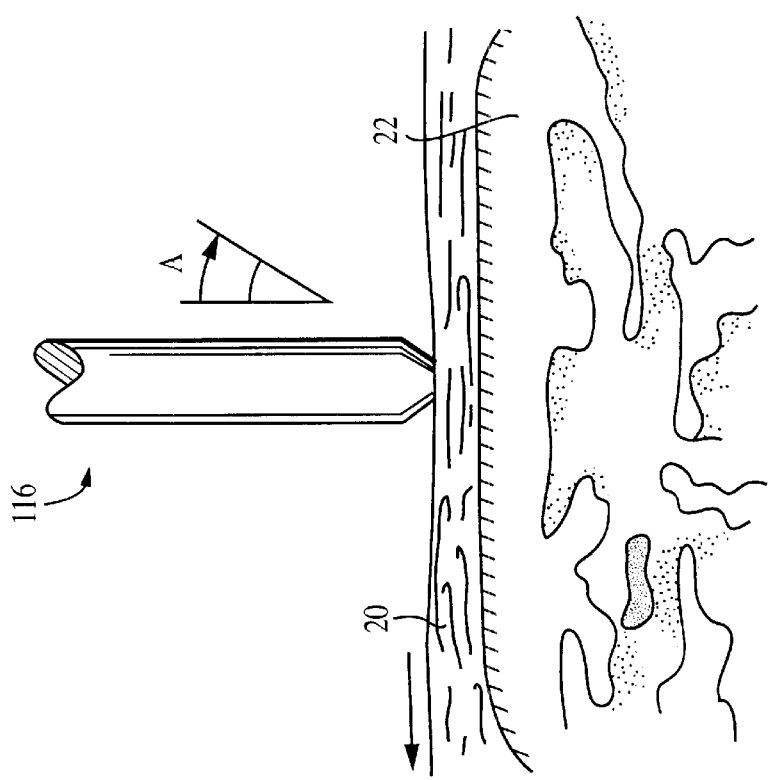
Figure 4C:
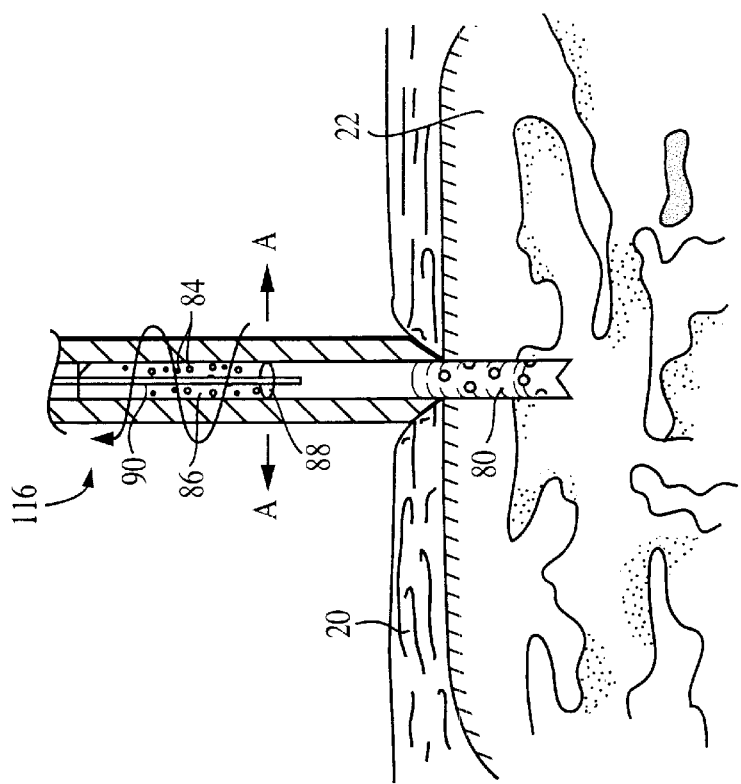
Figure 4B:
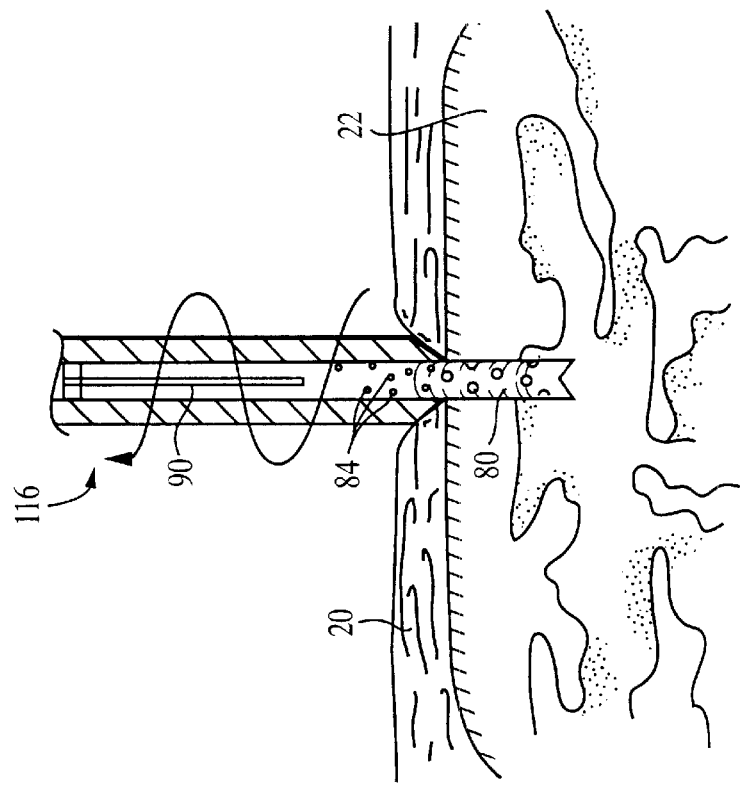
Figure 4E:
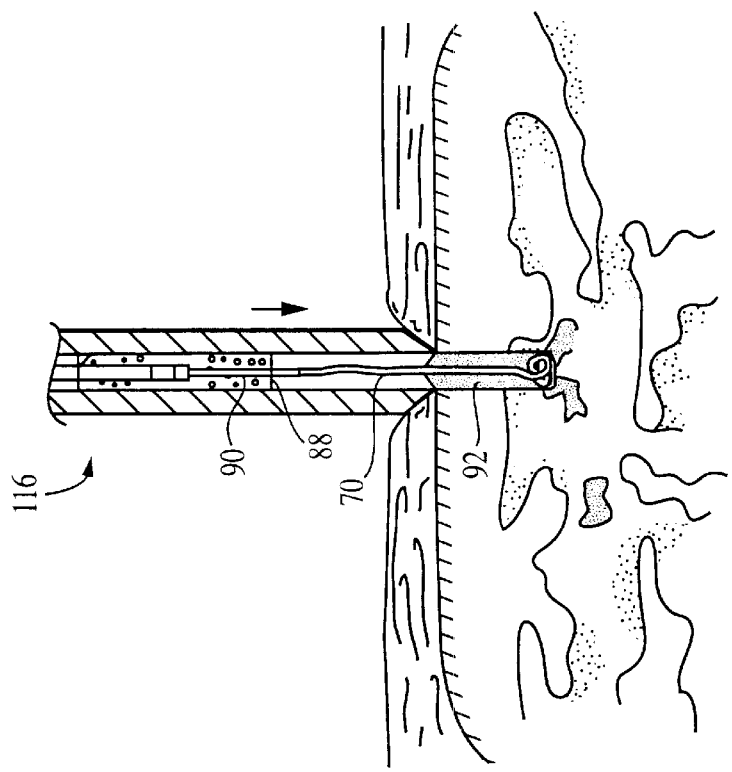
Figure 4D:
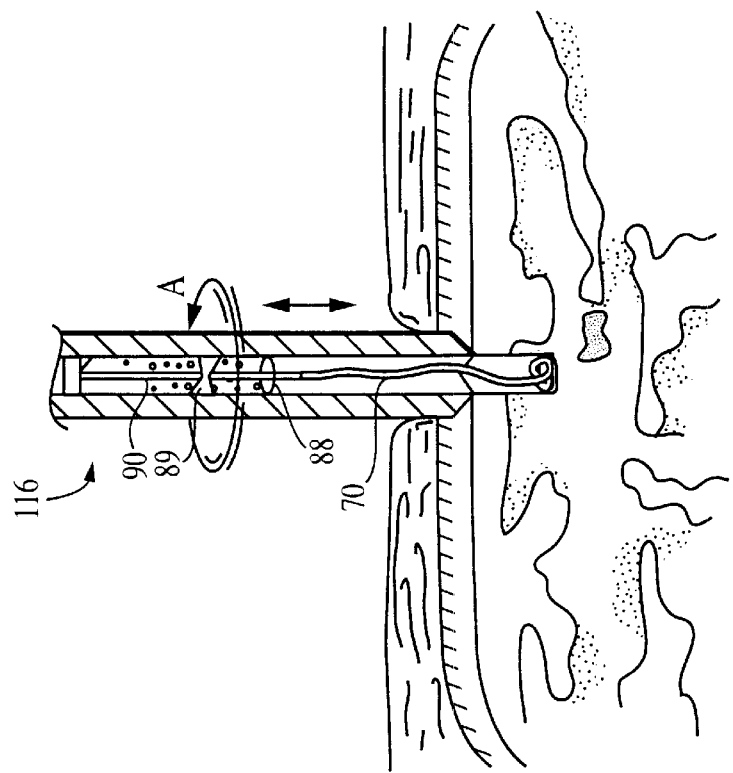
Figure 4G:
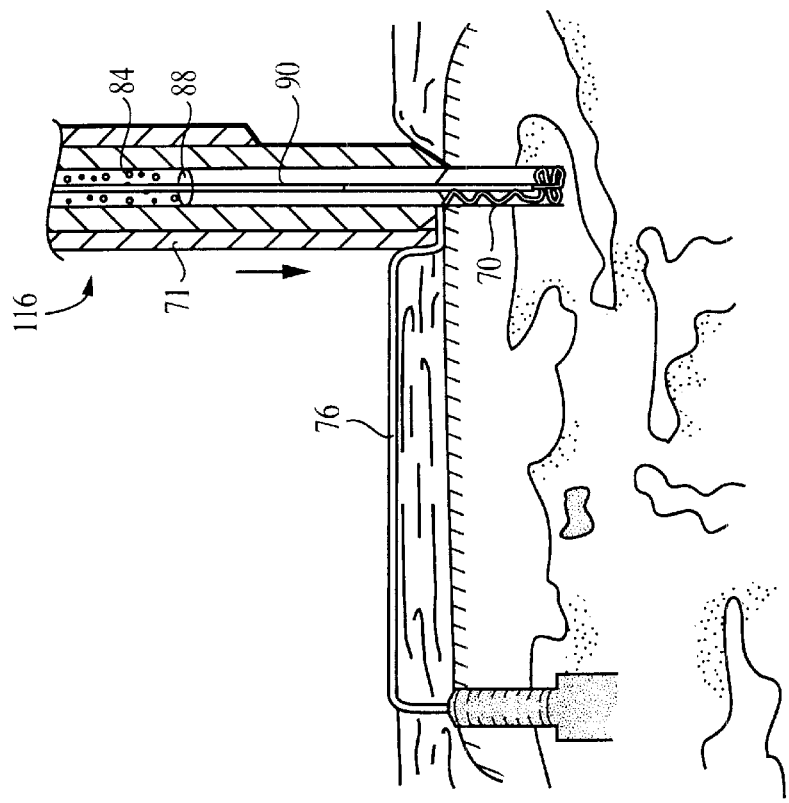
Figure 4F:
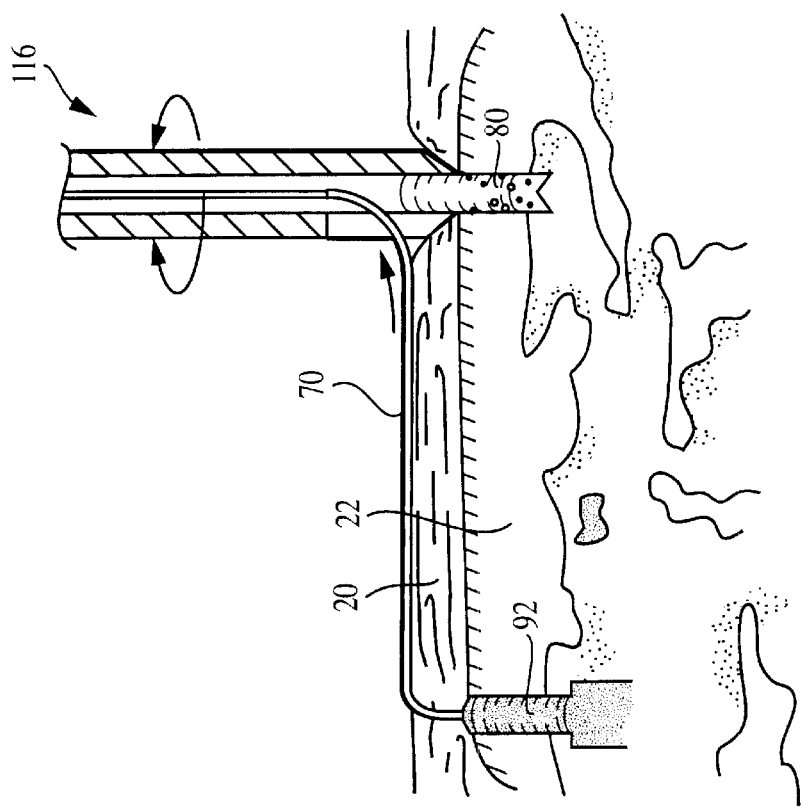
Figure 4I:
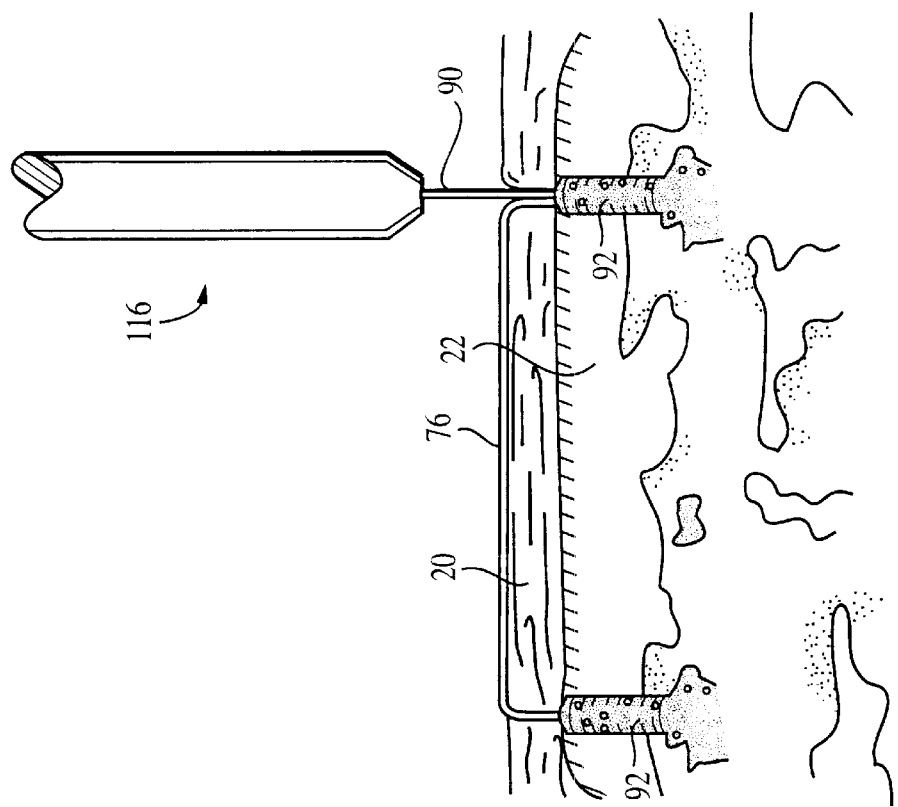
Figure 4H:
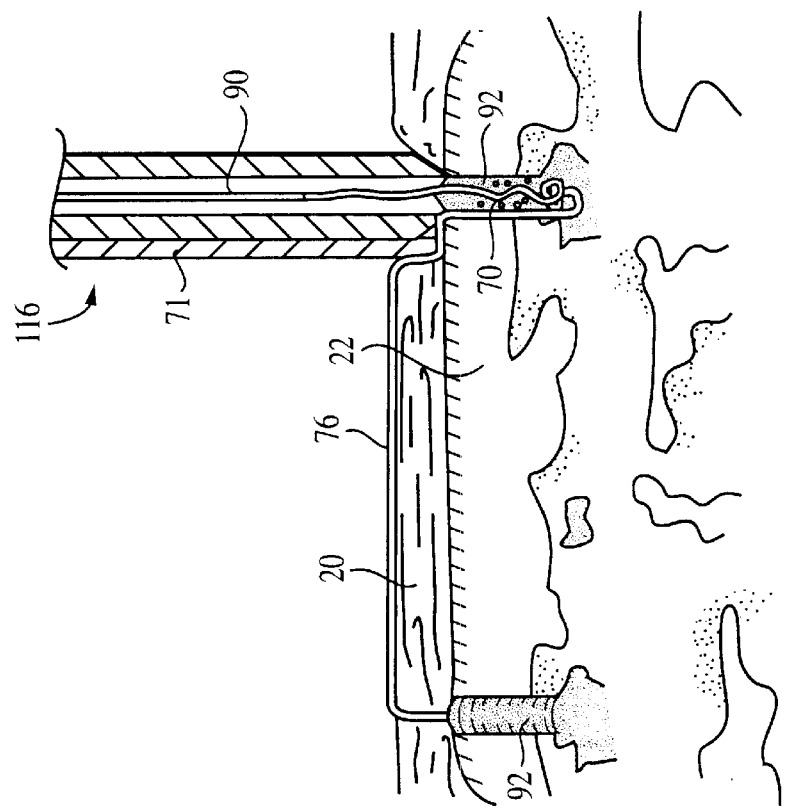
Figure 4J:
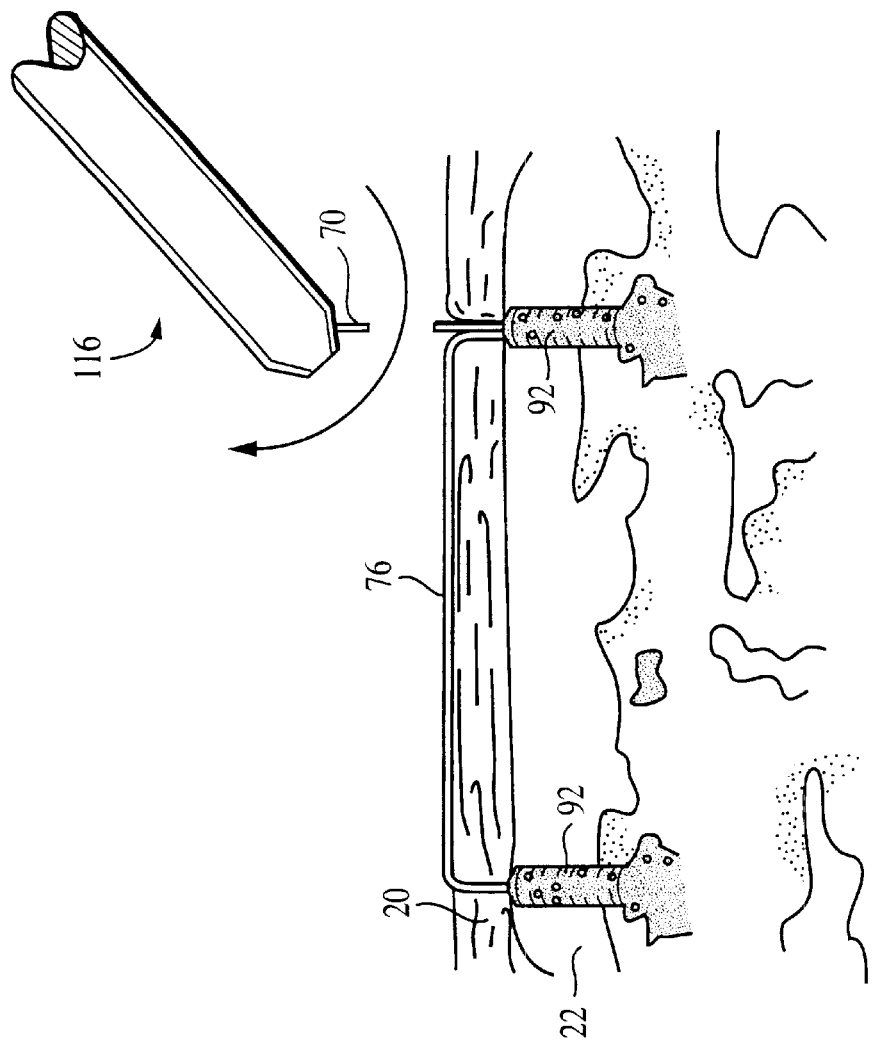

An alternative procedure for forming a row of stitches is shown in FIGS. 4–4G. In this procedure, the bone fragments and debris generated during cavity forming are incorporated into the polymer as a filler. It is noted that bone fragments and debris can be incorporated into the polymer in a similar manner in any of the procedures described herein. The procedure shown in FIGS. 4–4G is performed using a surgical device 116 that is similar to surgical device 16, except that it also includes a suction device for extracting bone fragments and debris from the cavity, and a mixing chamber and a mixing device, for incorporating the bone fragments and debris into the polymer.

Referring to FIGS. 4 and 4A, using surgical instrument 116 the soft tissue 20 is pierced and a cavity is drilled in the bone 22, as discussed above. In this embodiment, the cutting tool is a perforated drill 80 (similar to a grater), having a serrated tip 82. Because the drill tip is serrated, it is preferred that the surgical instrument 116 be held at an angle, rather than perpendicular to the surface of the soft tissue 20, as indicated by angle A in FIG. 4, until the soft tissue 20 has been pierced. During drilling, the resulting bone fragments and debris 84 are suctioned out of the cavity and up through the cannula of the drill, as indicated schematically in FIG. 4B. The bone fragments/debris are then retained in a temporary chamber 86, defined by the cylindrical cutting tool barrel and a balloon diaphragm 88, suspended on a needle 90, that is inflated at this point in the procedure (arrows A, FIG. 4C). As shown in FIG. 4D, the surgeon then delivers suture 70 through needle 90, while simultaneously adding polymer to chamber 86 and mixing the polymer with the bone fragments/debris 84 (arrow A). Using the air supply, the polymer is fed to chamber 86, in powder form, from a reservoir that is preloaded prior to surgery. Mixing can be performed using any desired mixing device, e.g., a mobius band 89 mounted on needle 90. The polymer is heated during or after mixing. Once the polymer has melted, the polymer/bone fragment mixture 92 is delivered from the temporary chamber 86 to the cavity by collapsing the diaphragm 88 so that the polymer mixture will flow into the cavity due to the force of gravity (FIG. 4E). The surgeon collapses the diaphragm by operating a switch on the surgical device which inflates and deflates the diaphragm, in the same manner that balloon catheters are conventionally actuated. The remaining steps of the procedure, shown in FIGS. 4F–4J, are conducted in the same manner as the steps shown in FIGS. 2E–2J and discussed above, except that bone fragments and debris are collected and mixed into the polymer each time a cavity is drilled.

Figure 5B:
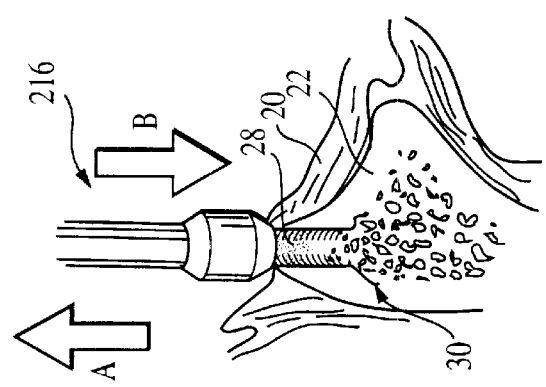
FIGS. 5–5F are diagrammatic views of a procedure for forming a sutureless polymeric anchor to fix soft tissue to bone.
Figure 5A:
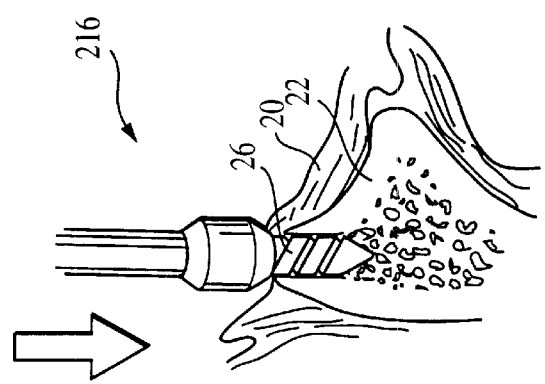
Figure 5:
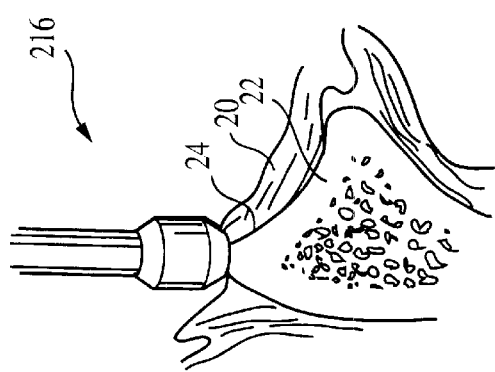
Figure 5C:
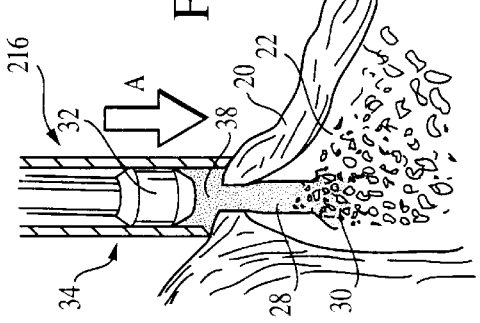
Figure 5D:
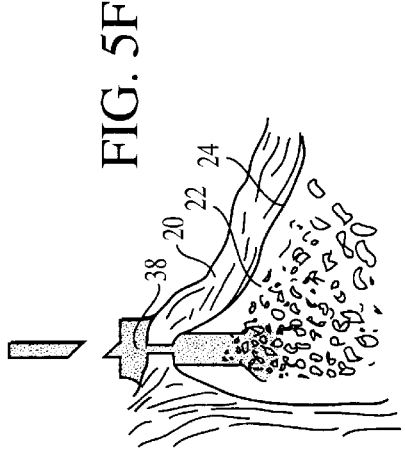
Figure 5E:
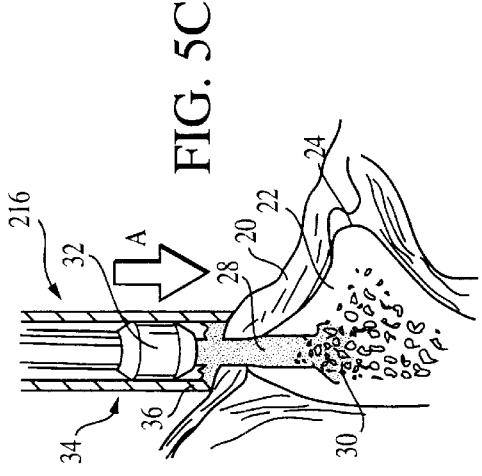
Figure 5F:
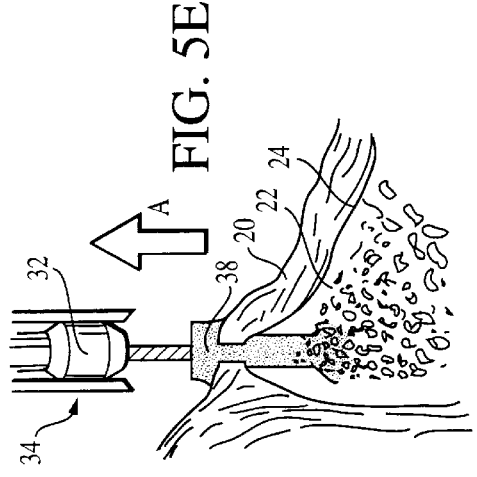

An alternate surgical procedure, used to form a single, bolt-like polymeric anchor, is shown in FIGS. 5–5F. This procedure utilizes a surgical instrument 216, which includes a cutting tool to pierce soft tissue and form a cavity in bone, a supply of polymer and a heating element to melt the polymer, a cannulated tube to guide the cutting tool and deliver the polymer to the cavity, and a compounder that is constructed to form a molding cavity for shaping the "head" of the bolt-like anchor.

Referring to FIGS. 5–5F, a surgical instrument 216 is pressed against the soft tissue 20, which is in turn pressed against the bone surface 24 (FIG. 5), and a cutting tool, e.g., a drill bit 26, is used to pierce soft tissue 20 and form a cavity in bone 22 (FIG. 5A). The cutting tool is then retracted (arrow A, FIG. 5B), and a molten polymer 28 (e.g., melted as described above) is injected into the cavity (arrow B, FIG. 5B) through a cannula of the surgical instrument 216.

Next, a compounder 34 (a part of surgical instrument 16 that has been retracted in previous steps) is extended (arrow A, FIG. 5C) so that the tip 36 of the compounder presses against soft tissue 20 to hold it against bone surface 24. Meanwhile, the cannulated head 32 of the surgical instrument 16, through which the polymer is delivered, is retracted a short distance so that, with the cylindrical wall of the compounder, it defines a small molding chamber. Polymer continues to be delivered through the cannula of the surgical instrument and this polymer fills the molding chamber to form a polymeric "bolt head" 38 (FIG. 5D). The bolt head 38 is integral with the polymer in the cavity, which extends through the soft tissue 20. Thus, the polymer forms a bolt-like anchor that secures the soft tissue to the bone (FIGS. 5E and 5F).

As shown in FIGS. 5E and 5F, the procedure is completed by removing the surgical instrument 16 (arrow A, FIG. 5E) and snipping any excess polymer off at the top of the bolt head. The manner in which the polymer is snipped off is not shown; if this step is necessary, it can be performed using a clipper attachment to the surgical instrument 16, or using a separate device such as a scalpel.

Figure 6:
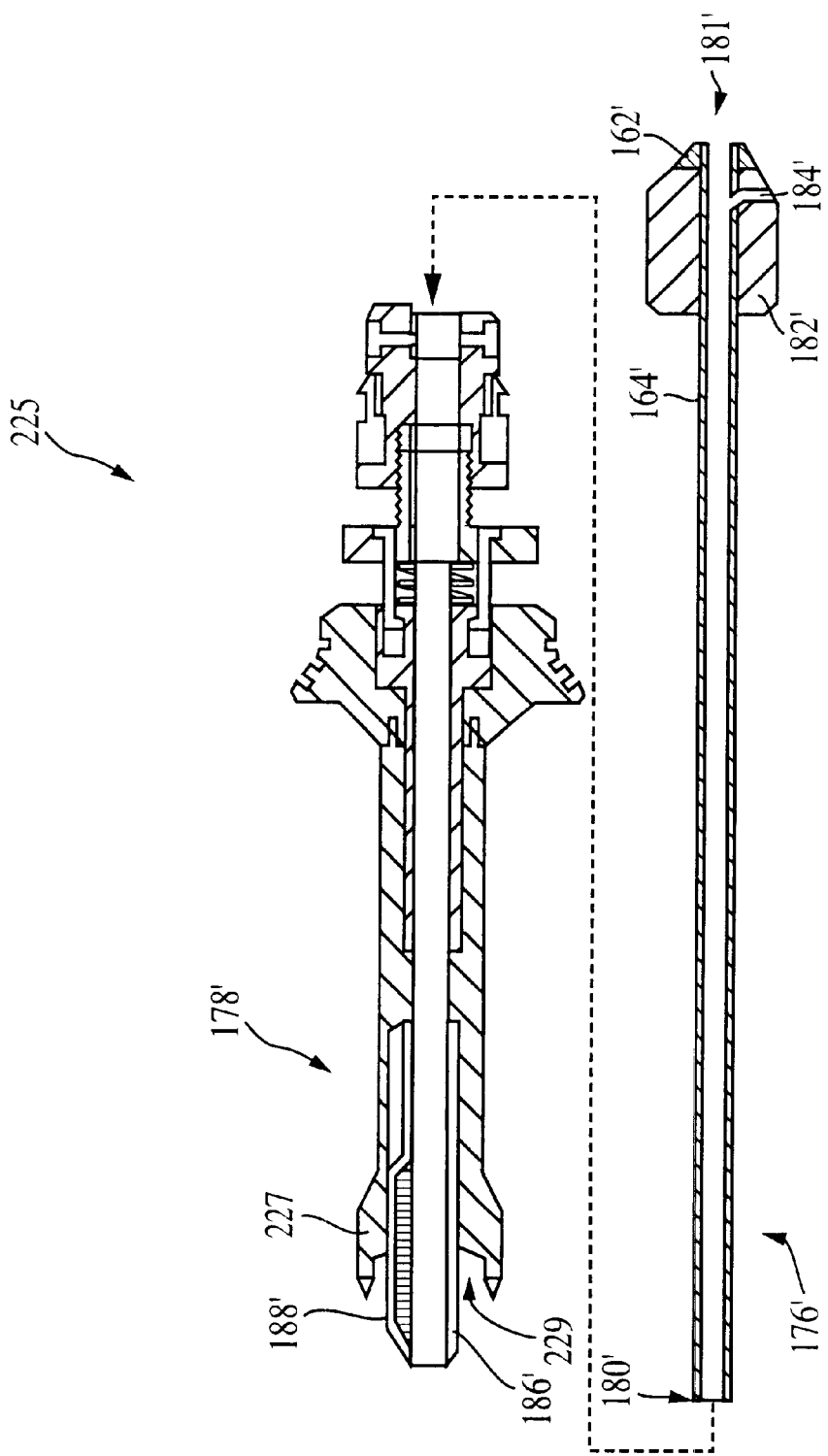
FIG. 6 is an exploded cross-sectional view of a surgical instrument attachment suitable for use in the procedure of FIGS. 5–5F.

The procedure shown in FIGS. 5–5F can be performed using an attachment 225, shown in FIG. 6, mounted on the handpiece 52 that is shown in FIGS. 3–3D and discussed above. The handpiece 52 can be used with a wide variety of interchangeable attachments, suitable for use in various procedures of the invention. For example, as shown in FIG. 7, the handpiece can be used with attachment 54 to perform a stitching procedure, with attachment 225 to form a bolt-like polymeric anchor using the procedure shown in FIGS. 5–5F, and with attachments 250 and 300 to perform soft tissue to soft tissue fixation procedures that will be described below.

Figure 6A:
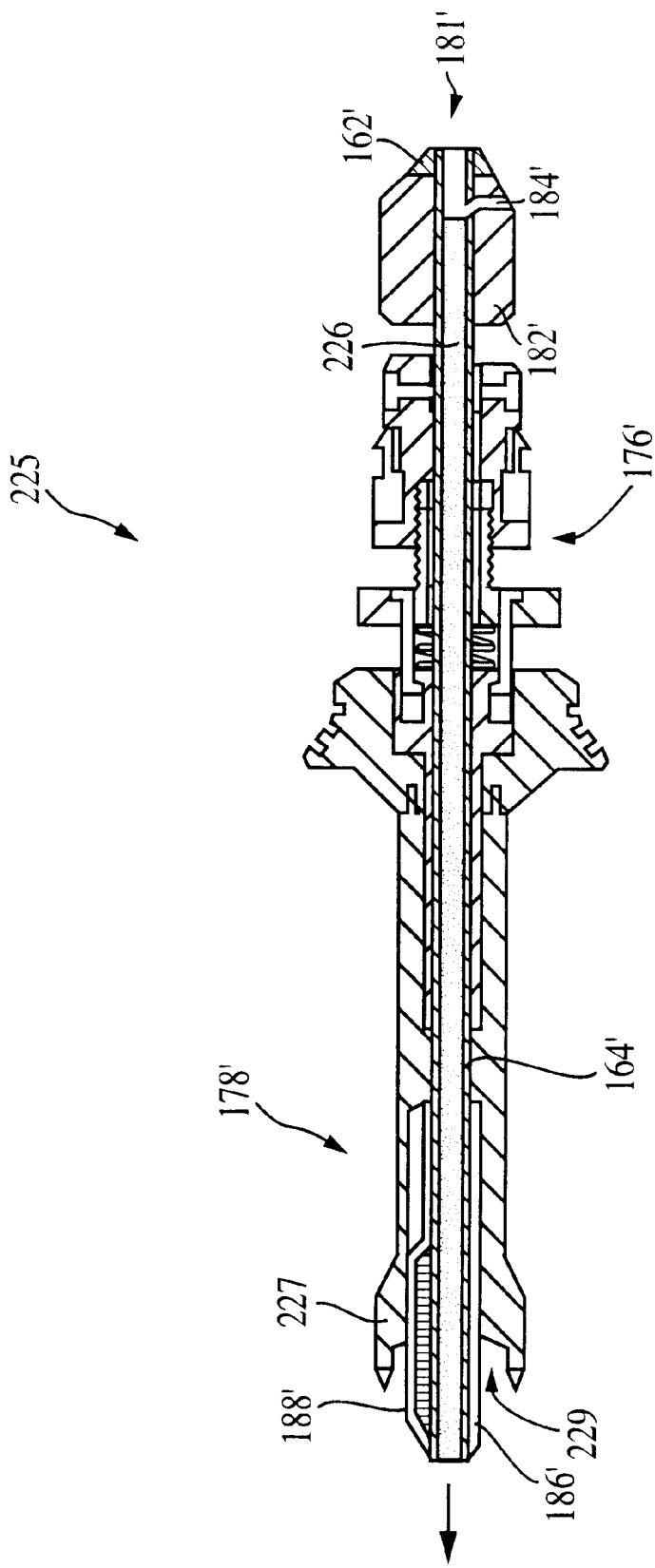
FIG. 6A is a cross-sectional view of the surgical instrument attachment of FIG. 6 assembled.

Attachment 225 is similar to attachment 54, discussed above, except that it does not include a chamber or cavity for receiving a polymer pellet. Instead, a polymer rod 226 (FIG. 6A) is advanced through the handpiece using the suture delivery function. The polymer rod 226 includes a grommet (not shown) at its distal end 228, to prevent gas from escaping through end 181'. Also, the guide/heating device 178' includes a compounder 227 which defines a molding chamber 229, as discussed above. The compounder 227 is moved axially by the surgeon as discussed above with reference to FIGS. 5C–5E.

In another embodiment, fixation methods are provided for attaching soft tissue to soft tissue. These fixation methods are suitable for use, for example, in laparoscopic surgery. Procedures and devices for soft tissue to soft tissue fixation are shown in FIGS. 8–11 and described below.

Figure 8B:
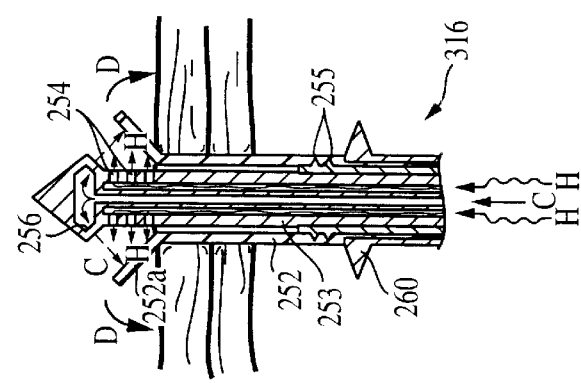
FIGS. 8–8F are diagrammatic views of a procedure for fixing soft tissue to soft tissue with a polymeric anchor.
FIG. 8G is a partial perspective view of the finished anchor.
Figure 8A:
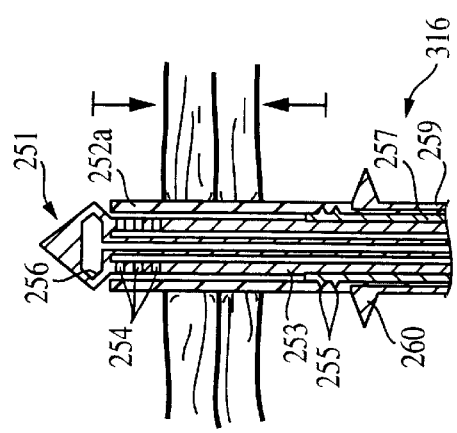
Figure 8:
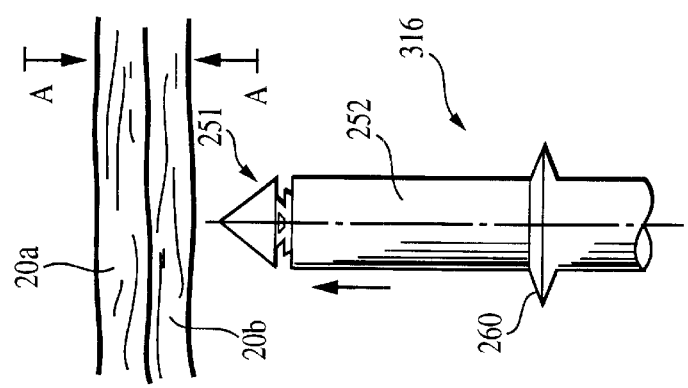
Figure 8E:
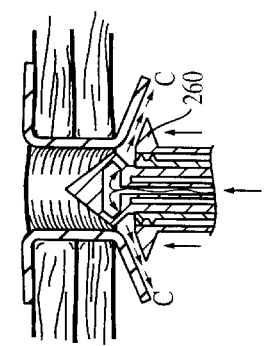
Figure 8D:
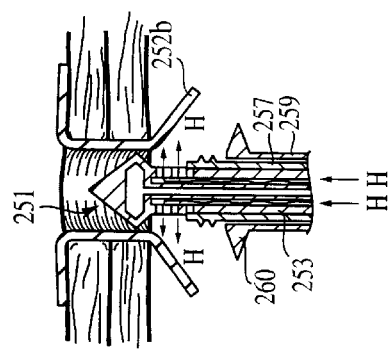
Figure 8C:
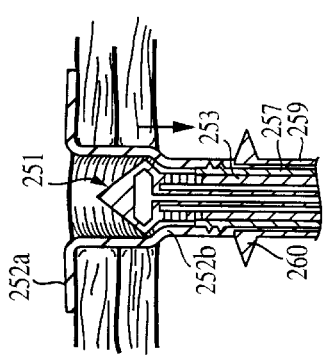
Figure 8G:
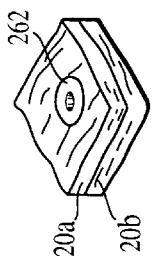
Figure 8F:
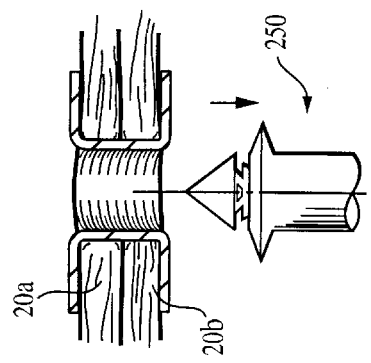
Figure 9:
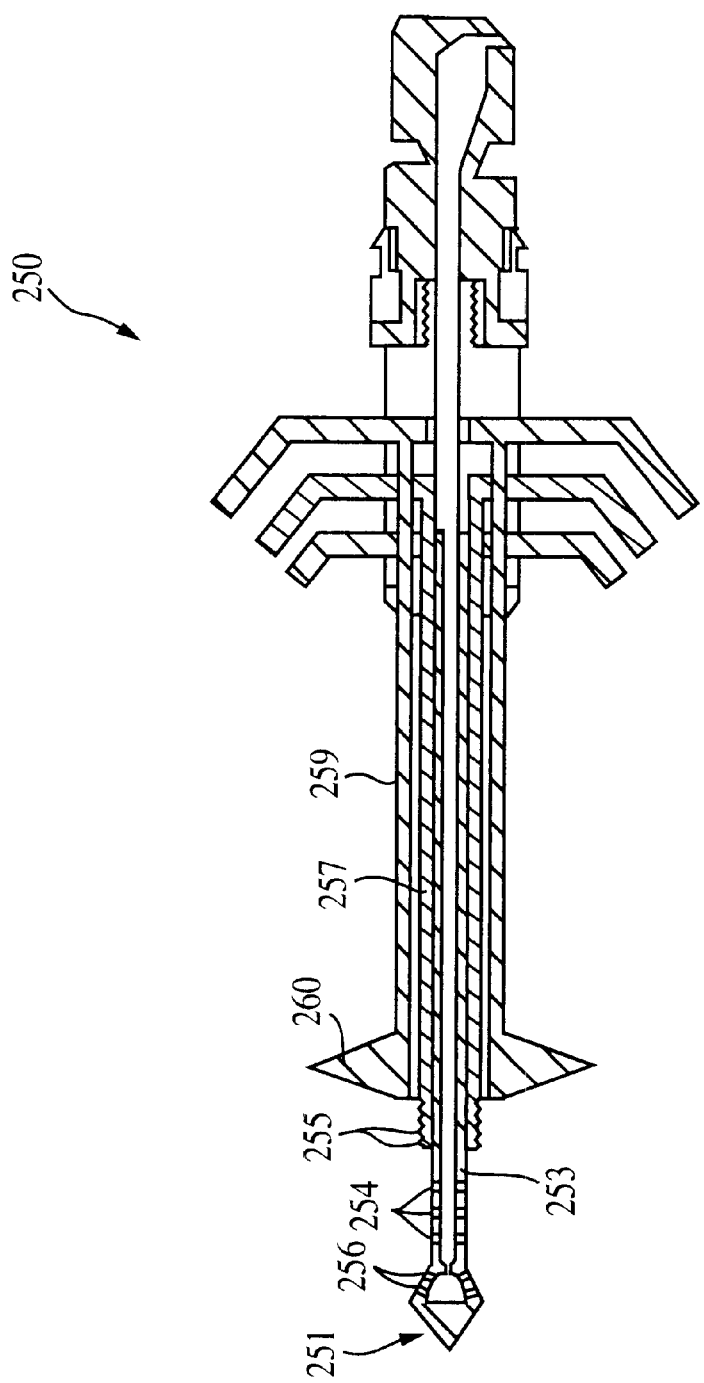
FIG. 9 is a cross-sectional view of a surgical instrument attachment suitable for use in the procedure of FIGS. 8–8F.

A first procedure, which forms a polymeric "rivet", is shown in FIGS. 8–8F. This procedure uses a surgical instrument 316, which generally includes an inner, axially movable tube having a sharp tip for piercing through soft tissue, and a cannulation in communication with a number of openings for delivery of hot and cold air from the inner tube. The surgical device also includes an outer tube, on which is mounted a polymeric sheath that will be softened and shaped by the delivered air to form the rivet, and a compounder, surrounding the outer tube, that includes a flange for directing the air and shaping the polymeric sheath into a rivet shape.

Referring to FIG. 8, two portions of soft tissue 20a, 20b, are compressed together (arrows A, FIG. 8), using known surgical techniques. Next, the tip 251 of an inner, axially movable tube 253 (FIG. 9) of surgical device 316 is punched through the soft tissue (FIG. 8A). A polymeric sheath 252 is mounted on outer tube 257, and a portion 252a of the polymeric sheath is carried through the soft tissue and out the other side. The polymeric sheath is held in place by ridges 255 on outer tube 257. Outer tube 257 is surrounded by compounder 259, the function of which will be described below.

Hot air (arrows H, FIG. 8B) is then directed out of side openings 254 of tip 251, and cold air (arrows C, FIG. 8B) is directed out of tip openings 256. The hot air melts the polymeric sheath, and the cold air forces it downward (arrows D, FIG. 8B) against the soft tissue (FIG. 8D). The hot air is generated at the tip due to the relationship between the air pressure being forced out of the tip and the size of side openings 254.

The inner tube 253 of instrument 250 is then withdrawn through the polymeric sheath until the side openings 254 are aligned with portion 252b of the polymeric sheath (FIG. 8C). Hot air is directed out through the side openings 254 (arrows H, FIG. 8D) to melt portion 252b. Flange 260 of compounder 259 is then pressed against portion 252b, while cold air is directed out through tip openings 256 (FIG. 8E), solidifying portion 252b in place against the soft tissue (FIG. 8F). The air is directed by flange 260, which also serves to press portion 252B against the soft tissue. The surgical instrument 316 is then withdrawn (FIG. 8F), leaving a rivet-like anchor 262 (FIG. 8G) to hold the soft tissue firmly together.

A surgical instrument attachment 250, for use with handpiece 52 to form a surgical instrument 316 suitable for performing the procedure shown in FIGS. 8–8F and described above, is shown in FIG. 9. Attachment 250 includes the components described above with reference to FIGS. 8–8F, and can be mounted on handpiece 52 in the same manner as attachment 54, discussed above.

Figure 10B:
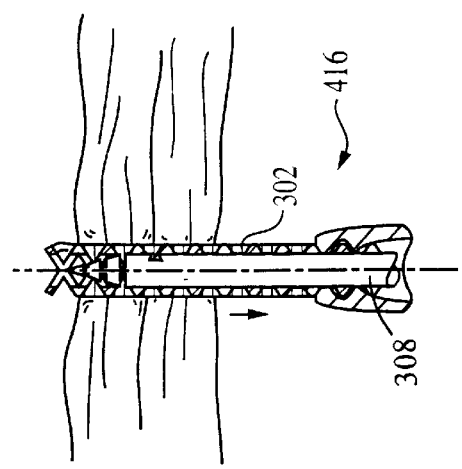
FIGS. 10–10H are diagrammatic views of an alternative procedure for fixing soft tissue to soft tissue with a polymeric anchor.
Figure 10A:
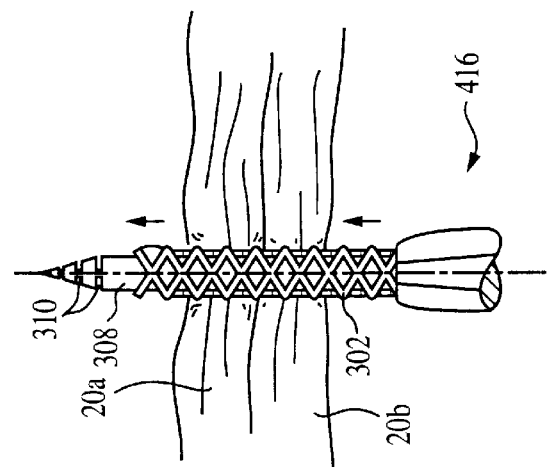
Figure 10:
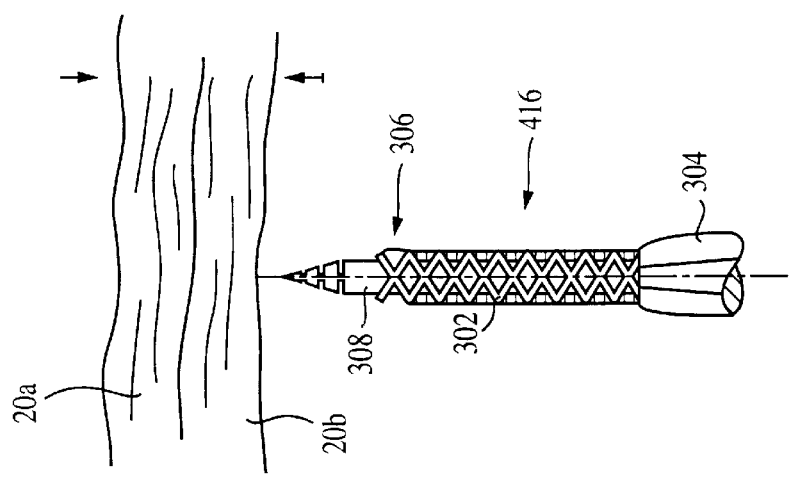
Figure 10C:
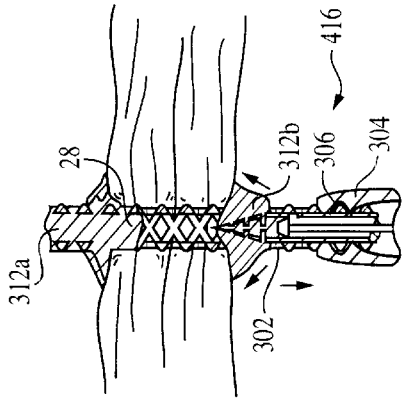
Figure 10D:
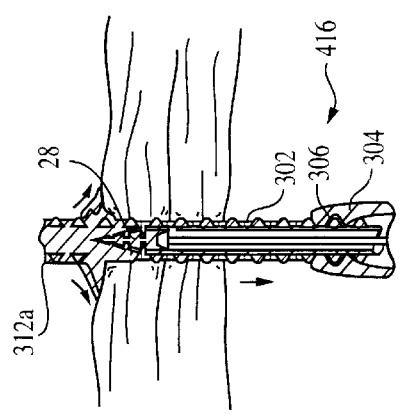
Figure 10E:
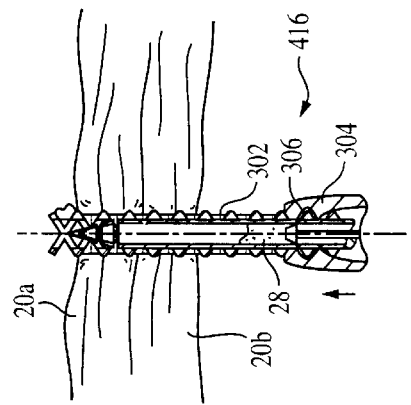
Figure 10F:
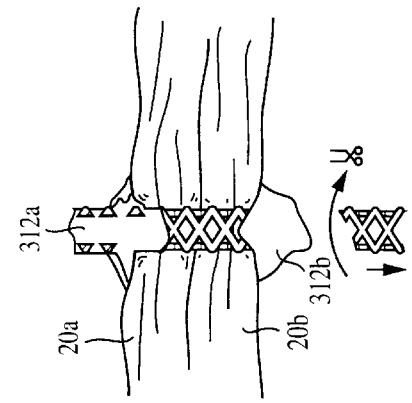
Figure 10G:
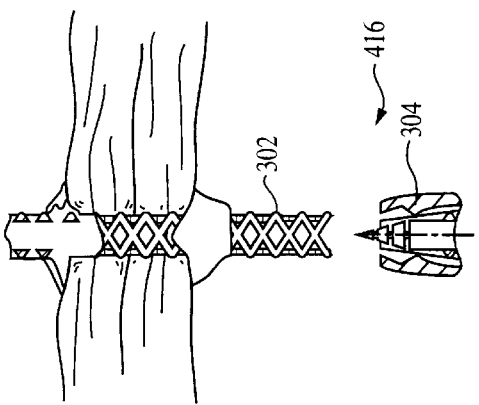
Figure 10H:
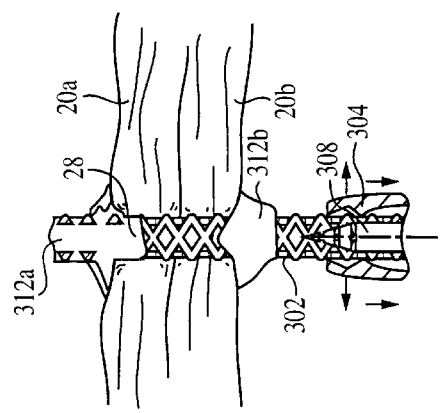

An alternative procedure for fixing soft tissue to soft tissue is shown in FIGS. 10–10H. This procedure is performed using a surgical instrument 416, which generally includes an inner tube having a sharp tip for piercing soft tissue and a cannulation for delivery of polymer. The surgical instrument 416 also includes a device for releasably mounting a porous sheath over the inner tube.

First, the soft tissue is compressed and is pierced by the sharp tip of surgical device 416 (FIGS. 10, 10A), as described above with reference to FIGS. 8 and 8A. The distal end 306 of a porous sheath 302, e.g., a braid or mesh, is gripped by a releasable chuck 304. A small polymer weld (not shown) near distal end 306 of the sheath keeps the sheath from being forced backwards during the piercing step.

The inner tube 308 is then withdrawn slightly (FIG. 10B), breaking the polymer weld and leaving the sheath 302 in position, and molten polymer 28 is delivered down the central cannulation of inner tube 308 and out of tip openings 310 (FIGS. 10C, 10D). The polymer bleeds out of the open end of sheath 302, and also out through the open structure of the mesh or braid, forming a "blob" 312a of polymer on top of the soft tissue and adhering the side walls of the sheath to the side walls of the opening in the soft tissue (FIG. 10D). The inner tube 308 is then withdrawn further, while continuing to deliver polymer through openings 310, filling the sheath with polymer and forming a "blob" 312b of polymer on the side of the soft tissue opposite blob 312a. Thus, the polymer defines a bolt-like anchor extending through the soft tissue.

To complete the procedure, the sheath is released from chuck 304 (FIG. 10G), the attachment 300 is removed, and any excess sheath material is snipped off (FIG. 10H).

Figure 11:
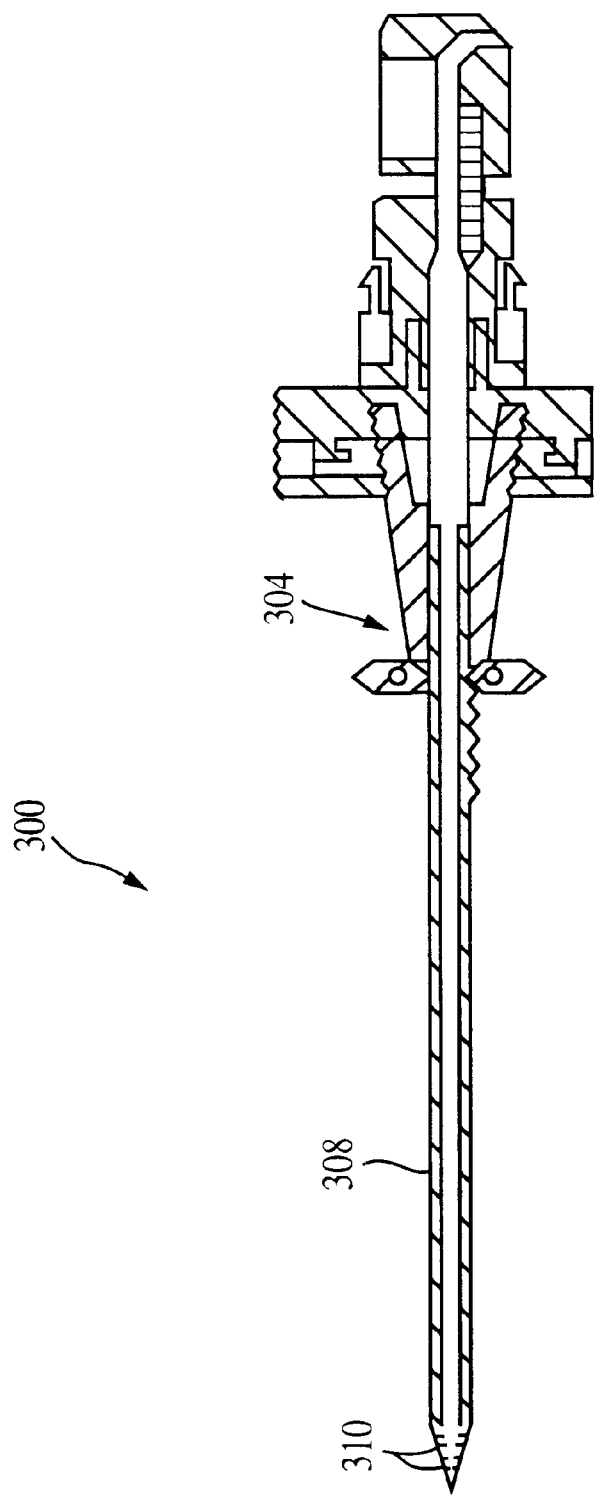
FIG. 11 is a cross-sectional view of a surgical instrument attachment suitable for use in the procedure of FIGS. 10–10H.

An attachment 300, suitable for use with handpiece 52 to form a surgical instrument 416, is shown in FIG. 11. Attachment 300 includes the components described above with reference to FIGS. 10–10H, and can be mounted on handpiece 52 in the same manner as attachment 54, discussed above.

Figure 12F:
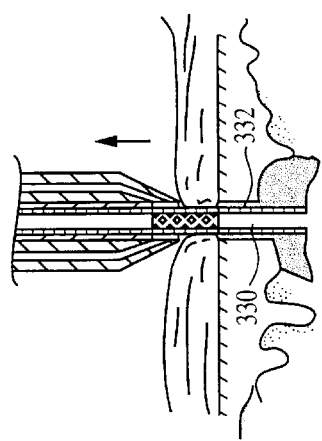
FIGS. 12–12I are diagrammatic views of another alternative procedure for fixing soft tissue to bone.
Figure 12G:
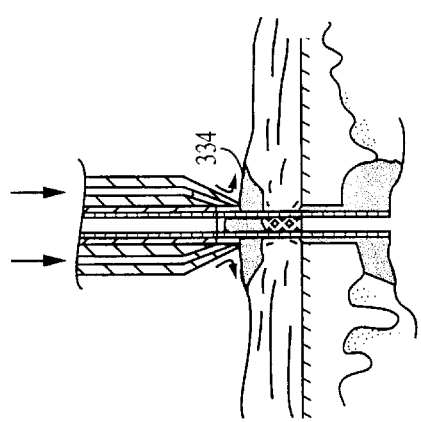
Figure 12H:
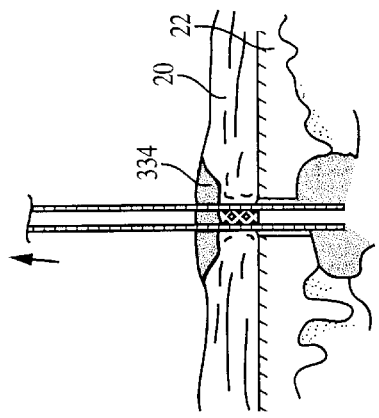
Figure 12I:
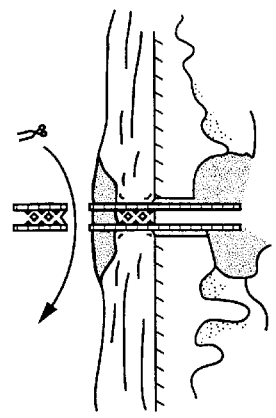

An alternative soft tissue to bone fixation procedure is shown in FIGS. 12–12I. In this procedure, a bone core is used to provide an osteoconductive medium within the polymeric anchor. This procedure is performed using a surgical instrument 516 that includes a cutting tool that is capable of forming in bone while leaving a bone core extending upward from the base of the opening. The surgical instrument 516 is constructed to deploy a tubular suture over the core, and deliver a polymer to the opening.

First, soft tissue is pierced, and a cavity is drilled (FIGS. 12–12B). The cavity is drilled using a cannulated cutting tool 331 that is constructed to leave a bone core 330 in the cavity (FIG. 12C). A flexible sleeve 332, e.g., a braided hollow suture, is deployed over the core 330, as shown in FIG. 12C. Polymer 28 is then delivered to the cavity (FIGS. 12D, 12E) around the sleeve 332 and core 330, and impregnates the sleeve 332. More polymer is delivered, while retracting the surgical instrument (FIGS. 12F, 12G), to form a blob 334 on the surface of the soft tissue, anchoring the soft tissue against the bone (FIG. 12H). Any excess sleeve material is then snipped off (FIG. 12I). The presence of the bone core in the anchor will tend to increase bone remodeling, and thus the suture may become embedded in bone more rapidly than would occur if the bone core were not present.

Another alternative soft tissue to bone fixation procedure is shown in FIGS. 13–13J. In this procedure, a suture is anchored in a cavity, using polymer, and a fixation device 340 is deployed around, and adhered to, the suture above the soft tissue to mechanically clamp the soft tissue in place. This procedure provides a low-profile anchor that may be useful in low clearance areas to prevent impingement. This procedure is performed using a surgical instrument 616 that includes a cutting tool to pierce soft tissue and form a cavity in underlying bone, a cannulated tube for delivery of a suture and polymer to the cavity and deployment of a fixation device around the suture, and a compounder to press the soft tissue against the bone and the fixation device against the soft tissue.

As shown in FIGS. 13–13C, soft tissue is pierced, a cavity is formed, and suture and polymer are delivered as discussed above, e.g., with regard to the procedures shown in FIGS. 2–2K. Next, while holding down the soft tissue with a compounder 335 (FIG. 13D), an expandable fixation device 340 is deployed around the suture to clamp the soft tissue in place (FIGS. 13E–13G). The expandable fixation device 340 includes a central region 341, having a bore 346, and a plurality of wings 354 extending radially from the central region. Wings 354 are joined to central region 341 by a plastic hinge having a memory that biases the wings toward an open position (FIG. 13F), while allowing the wings to be moved to a compressed position (FIG. 13E) so that the device can be deployed through a cannula. Thus, fixation device 340 is compressed and placed in delivery tube 339, with a suture 347 threaded through central bore 346, and is deployed by pressing down on the fixation device 340 with a cannulated probe 343 (FIGS. 13E–G). As the fixation device exits the compounder 335, the wings 354 expand outward to their normal position (FIG. 13F), and the compounder 335 presses the fixation device 340 down to flatten it against the soft tissue (FIG. 13G). Barbs 342 on wings 354 hold the fixation device 340 in place against the soft tissue, in its flattened position. The suture 347 is then snipped (FIG. 13H), and a blob of polymer 344 is delivered on top of the fixation device to cover bore 346 and adhere to the suture, anchoring the fixation device in place (FIGS. 13I and 13J). Preferably, fixation device 340 is formed of a resorbable plastic.

Many different types of cutting tools may be used in the procedures of the invention. Generally, it is preferred that the cutting tool not compact the bone fragments and debris into the side wall of the cavity, as this may impede infiltration of the polymer into the trabecular network surrounding the cavity. Thus, for example, a twist drill is generally preferred to a compacting drill. Some of the types of cutting tools that may be used are discussed below.

Referring to FIGS. 14–14D, the cutting tool may be a drill bit 94 that is consumable, i.e., the drill bit is formed of a polymer that melts during drilling (FIGS. 14B–14C), as a result of the heat generated by friction, to fill the cavity with molten polymer. A suture 95 is attached to the drill bit 94, so that the suture is delivered with the polymer and left behind when the surgical instrument is retracted (FIG. 14D). In this case, it is generally preferred that the drill bit be coated with a very thin layer of porous ceramic, just thick enough to provide the drill with sufficient hardness to penetrate the cortical bone and sufficiently thin so that the polymer will be able to melt during drilling. The ceramic can be applied by firing, plasma coating, deposition, or other suitable methods. Alternatively, a thin, hollow ceramic preform can be formed and then filled with polymer. Preferred polymers have a sufficiently low melting point to melt under drilling friction, and sufficient strength to contribute mechanical strength to the drill bit. The suture 95 may be conductive, to allow it to serve as a heating element to assist in melting the polymer if drilling does not generate sufficient heat.

FIGS. 15–20 show various suitable cutting tool geometries.

FIGS. 15 and 15A show a perforated drill 100, including openings 96 and sheath 98. Perforated drill 100 is useful when bone fragments/debris are to be collected for incorporation into the polymer (as discussed above with reference to FIGS. 4–4J), and when it is necessary that the cutting tool oscillate, rather than rotating (e.g., to avoid cutting or breaking a suture between stitches).

FIGS. 16–16A show a configured head 102, having a blade 103 that includes an opening 104 through which a suture can be threaded for delivery, and a barrel 105 defining a lumen 106 for suture and polymer delivery. Lumen 106 is generally substantially coaxial with opening 104.

Figure 17:
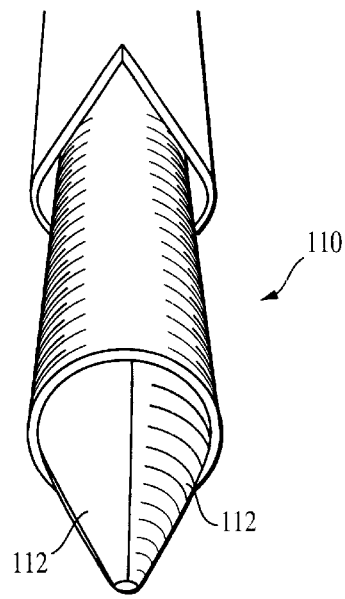
FIGS. 17 and 17A are perspective views of an alternative cutting tool in closed and open positions, respectively.
Figure 17A:
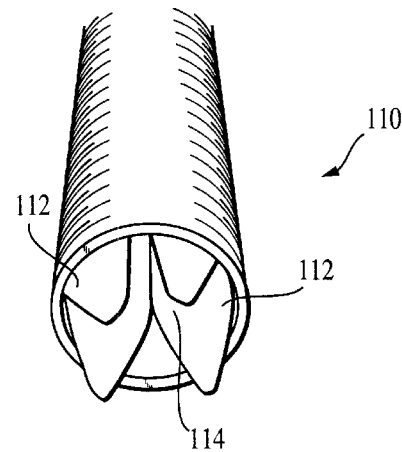

FIGS. 17–17A show an awl 110. Awl 110 includes a plurality of retractable "petals" 112, which when closed (as shown in FIG. 17) define a drill tip. When open (as shown in FIG. 17A), the petals 112 allow polymer and suture to be delivered through lumen 114. The petals may be opened and closed using a spring mechanism (not shown) or other suitable actuator.

Figure 18:
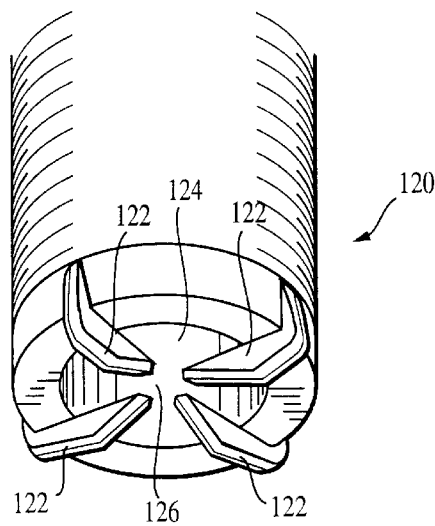
FIGS. 18 and 18A are perspective and front views, respectively, of an alternative cutting tool.
Figure 18A:
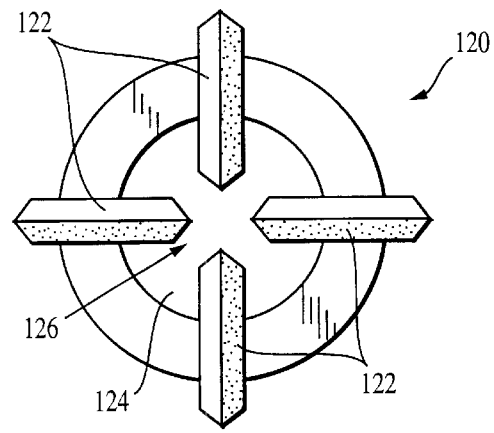

FIGS. 18–18A show a cutting head 120 having blades 122 radially extending crosswise across an open lumen 124. An open area between the blade tips defines an eyelet 126, to allow delivery of a knotted suture.

Figure 19:
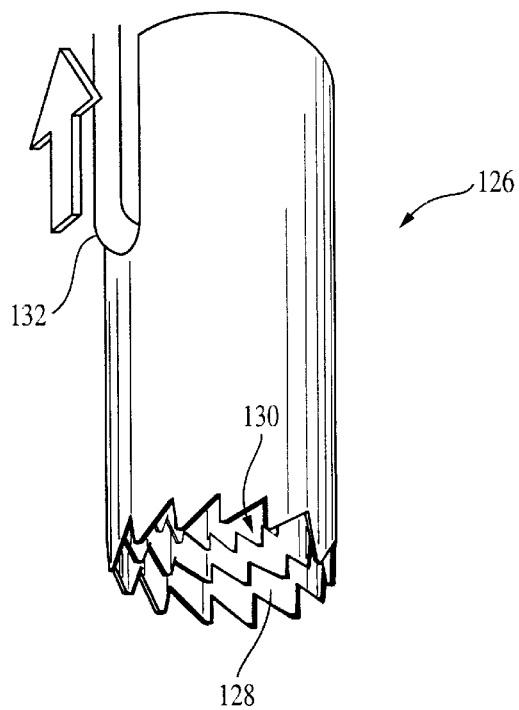
FIG. 19 is a perspective view of an alternative cutting tool.

FIG. 19 shows a borer 126, including a plurality of serrated cutting/abrading tubes 128, a central lumen 130 through which polymer and suture can be delivered, and an extraction tube 132 for drawing bone fragments/debris away from the cutting site by suction. If desired, the contents of the extraction tube can be fed into the barrel of the borer, or elsewhere into the surgical instrument, at a location where the bone fragments/debris can be blended into the polymer prior to delivery of the polymer.

Figure 20:
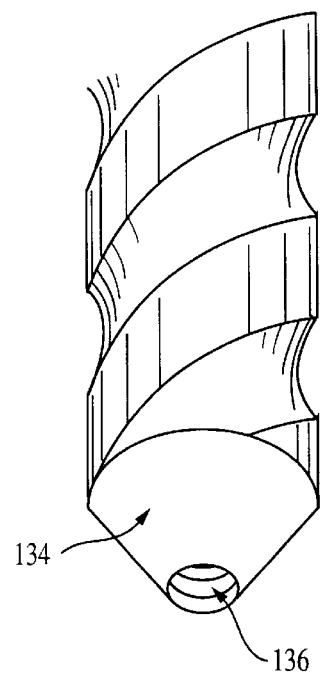
FIGS. 20 and 20A are perspective and cross-sectional views, respectively, of an alternative cutting tool.
Figure 20A:
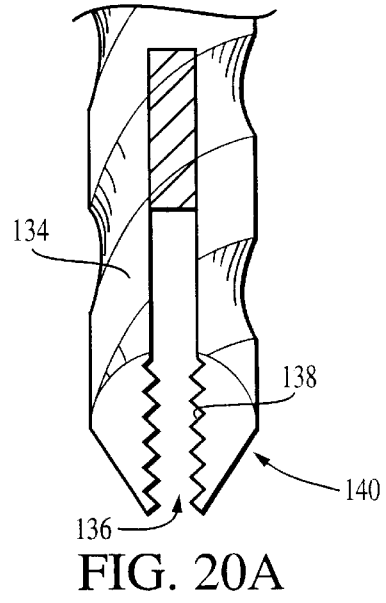
Figure 20B:
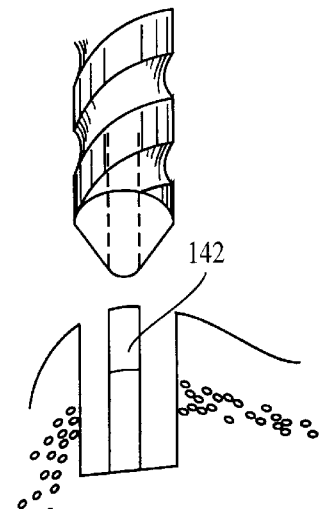
FIG. 20B is a diagrammatic cross-sectional view showing the cutting tool of FIGS. 20–20A in use.

FIGS. 20–20B show a twist drill bit 134 having a delivery channel 136 for delivery of polymer and suture. The inner wall 138 of the delivery channel, in the vicinity of the tip 140 of the drill bit, may be abrasive, so as to break up the bone "core" 142 (FIG. 20B) if a bone core is not desired.

Cutting can also be accomplished using other techniques, such as laser, ultrasonic or water jet cutting. For example, water jet cutting could be performed using the saline supply that is present in the operating room. In this embodiment, a dynamo generator would be included in the surgical instrument, to power the water jet, and the surgical instrument would include an adaptor to allow the saline supply to be plugged in to the surgical instrument. Other suitable techniques include crush indentation, hot needle drilling, thermally degrading the bone, e.g., with RF ablation, and cryogenic freeze fracturing. In some implementations, it is preferred that the cutting method be capable of forming a very small diameter cavity, e.g., less than 2 mm and preferably less than 1.5 mm. To form such a small diameter cavity, cutting may be performed using microtooling. Because a conventional bone anchor is not needed in many of the procedures of the invention, the cavity can be made smaller than the diameter of such anchors, thereby preserving more cortical bone, limiting trauma, and potentially improving the pull-out strength of the anchor. When a very small diameter cavity is used, e.g., less than 3 mm, the cortical bone will tend to grow back over the cavity, further increasing the strength of the anchor.

While in the embodiments discussed above the polymer is generally provided in the form of a powder or pellets, the polymer may be provided in any desired form. For example, the polymer may be contained in a cartridge that can be heated using equipment that is available in the operating room, e.g., an autoclave or heated bath. Thus, the cartridge can be preheated prior to surgery, and then inserted into a surgical instrument (not shown) that is adapted to puncture the cartridge for delivery of the polymer. The polymer may also be provided as a rod, or in the form of fibers or strands to increase its surface area and thereby decrease melting time.

The polymer can be heated using any suitable method. Preferred methods will heat the polymer in a controlled manner, to a temperature just above its melting temperature, to avoid overheating and possible thermal trauma to the tissue and bone at the delivery site. To expedite the surgical procedure, it is preferred that heating occur within 2 minutes or less, unless the polymer is provided in a cartridge and is pre-heated, e.g., in an autoclave. One suitable method is to provide a heating element in the surgical instrument, as discussed above. Preferably the heating element is thermostatically controlled to prevent overheating of the polymer. Other suitable heating methods include ultrasound (which may also be used to form the cavity), use of the drive mechanism of the surgical instrument to heat the polymer, use of a conductive suture embedded in the polymer as a heating filament, laser (e.g., by including an indicator dye in the polymer and using a laser frequency that would not burn the tissue at the delivery site but would melt the polymer), and radio frequency and induction heating.

The suture material, if a suture is used, may be resorbable or non-resorbable. It is generally preferred that the suture material be braided, rather than monofilamentary, for greater surface area and surface roughness, to enhance pull-out strength. However, monofilament may be used if desired. A loose braid is generally preferred, as the spaces in the braid enhance polymer infiltration. A "bird's nest" arrangement of suture can also be formed by feeding suture out into the cavity and allowing it to pile up loosely in the cavity. Preferably, the suture does not include a polymeric coating. Suitable suture materials include polyesters, polyamides, e.g. Nylon, polybutester, polyglycolic acid, polyglyconate, poly-L-lactic acid and polydioxanone. It is generally preferred that the suture have a high tensile strength, i.e., sufficient strength so that the mode of failure during pull-out testing is not premature suture failure.

The suture may also include any desired feature or augmentation. For example, the suture may include one or more of the suture augmentations shown in FIGS. 21–21G, i.e., a knot 400 or knot bundle 402 (FIGS. 21 and 21D), a sphere 404 (FIGS. 21C and 21E), a shaped element 406, e.g., a larger diameter portion (FIG. 21A), a flexible 4-way connector 408 (FIG. 21B) or a t-bar 412 (FIG. 21G), or a plurality of barbs 410 (FIG. 21F). If positioned on top of the soft tissue after the suture is anchored in place, the suture augmentations shown in FIGS. 2I–21G may secure the soft tissue in place against the bone. If positioned in the cavity and surrounded by polymer, these features may increase the resistance of the suture to pull-out. Other features that will provide these or other functions may also be used.

Suitable polymers are thermoplastics that are acceptable for use in the body and can be delivered to a surgical site in a molten state. Preferably, the polymer will have a relatively low melting temperature to prevent thermal damage to tissue and bone during injection. For optimal deliverability, it is generally preferred that the polymer have an inherent viscosity of greater than about 0.6 dl/g, preferably about 0.6 to 0.7 dl/g, and an average molecular weight of greater than about 60,000 Mw, preferably about 60,000–70,000 Mw. The inherent viscosity is measured in chloroform, using the test described at col. 4, lines 33–36 of U.S. Pat. No. 5,679,723, which is incorporated herein by reference.

Preferably, the polymer used includes a resorbable polymer, e.g., polycaprolactone (PCL), which will slowly resorb during the natural healing process. The polymer may also include a non-resorbable polymer, e.g., polypropylene, polyacetal, polyethylene or polyurethane. The polymer may also include a blend of different resorbable polymers that resorb at different rates, e.g., blends of two or more of the following polymers: polycaprolactone (PCL), poly-l-lactic acid, poly-DL-lactic acid, polyglycolic acid, polydioxanone, polyglyconate, polytrimethylene carbonate, and copolymers of poly-L-lactic acid, poly-DL-lactic acid, polyglycolic acid, polydioxanone, polyglyconate, polytrimethylene carbonate, poly(hydroxyalkonates) (PHB, PHO, PHV), polyorthoesters, polyanhydrides, poly(pseudo-amino acids), poly(cyanoacrylates), poly(ester-anhydrides), polyoxalates, and polysaccharides. Other suitable polymers include poly-4-hydroxybutyrate (4PHB) and poly(alkylene oxalates).

As the polymer resorbs, the remaining, porous polymer resembles the trabecular network and thus encourages infiltration of osteoclasts, which cause breakdown of the polymer, and osteoblasts, which generate new bone. To encourage bone growth into the polymer, it is preferred that the polymer include an osteoconductive filler, e.g., hydroxyapatites (HA), calcium sulfates, tricalcium phosphates, bioactive glasses, aragonite, calcite, and mixtures of these fillers. A suitable level of osteoconductive filler will encourage bone growth without an unacceptable reduction in the deliverability of the polymer. Preferred levels are generally from about 0 to 40% by volume, most preferably about 30 to 40% by volume. Instead of or in addition to a conventional osteoconductive filler, the polymer may include bone fragments and debris, as discussed above. If bone fragments are used without another filler, it is generally preferred that the polymer include from about 0 to 60% bone fragments by weight, more preferably about 20 to 50% by weight.

The procedures discussed above may be used in many types of soft tissue fixation, including rotator cuff repair; instability repairs of the shoulder (e.g., SLAP, Bankart lesions, labral reattachment); repair or supplementation of anchors, screws and interference screws for attaching ACL autografts and allografts (e.g., bone-patella tendon-bone, Semigracilis, tendinosis, quadriceps autograft); and ACL repairs or revisions (e.g., where there is micromovement due to loosening of the fixation means and subsequent movement of the graft, or as a sealant to eliminate synovium fluid flow into bone hole cavities in ACL repair).

Endoscopic delivery of polymer may also be used in other applications, such as chondral repair, filling of harvest site defects in mosaicplasty, as an autograft diluent, refixation of small bony fragments, repair of osteochondritis dessicans (OCD) (i.e., by using injectable polymer to endoscopically reattach a loose flake of bone or cartilage, rather than pinning the flake in place), for spinal fusions, meniscal repair, fracture repair of non-load bearing bones, supplementation or augmentation of cancellous/cortical screws for long bone fractures especially in compromised or deficient bone, supplementation or augmentation of suture anchoring devices, in laparoscopic procedures to re-attach soft tissue to soft tissue or soft tissue to bone, and plastic surgery to aid in facial reconstruction.

Anchors of the invention generally provide good pull-out strengths. Pull-out strength will vary depending upon the suture, suture augmentation, number of sutures, and polymer used. For example, reduced pull-out strengths will be observed if a relatively weak suture material is used and the mode of failure is breakage of the suture. However, preferred anchors of the invention generally provide pull-out strengths of at least 150 Newtons, with some anchors providing strengths in excess of 300 Newtons, when tested in accordance with either of the test procedures (Test Procedures 1 and 2) described below. Pull-out strength is measured on cadaveric samples (shoulders) and on sawbone blocks (artificial bone), using the following test procedures.

PULL-OUT TEST PROCEDURES

Test Procedure 1

Cadaveric Samples

All of the shoulders used would be harvested from fresh specimens, i.e., unpreserved, and stored at approximately –10 degrees Celsius until necessary for testing. Before testing, the specimens would be allowed to thaw to room temperature before dissecting and sample preparation.

The humerus would be prepared for the repair of a rotator cuff tear at the bony site. A cavity would be drilled to a depth of about 10 mm using a twist drill bit having a diameter of 3.3 mm. A suture, e.g., Spectra thread or similar suture material, would be delivered to the cavity, and the cavity would be filled with polymer. The polymer would be allowed to harden/set, after which the sample would be placed in an Instron servo-hydraulic testing machine, with the suture orientated parallel in relationship to the force applied by the testing machine.

The samples would be held in an appropriate vice/clamp which is itself attached to a 3-axis vice to permit the precise orientation of the samples being tested, using an appropriate Instron servo-hydraulic testing machine and associated Instron Max software, at a displacement rate of 8.5 mm/sec.

Test Procedure 2

Sawbone Block Samples

Samples would be prepared and tested as described above in Test Procedure 1, except that instead of a cadaveric humerus, the anchor would be formed in a sawbone block. A suitable sawbone block material is commercially available from Pacific Research, under the tradename "Sawbones".

Other embodiments are within the claims.

For example, although in most of the embodiments discussed above polymer is used as a substitute for a conventional bone anchor, in some cases it may be desirable to use the polymer to supplement the anchoring provided by a conventional anchor, e.g., by applying the polymer on top of or around the anchor when the anchor is placed. This option could be useful, for example, in cases in which the surgeon chooses to use a conventional anchor and the patient will be on an aggressive rehabilitation schedule.

Also, in some applications bone fragments harvested at one site may be mixed with polymer and injected at a second site in the same patient. This procedure may be used, for example, in cases in which the bone at the injection site is diseased or compromised, and fresh bone is desired as an autologous filler. In addition, bone fragments can be mixed into polymer within the cavity that is being formed, rather than extracting the bone fragments first as described above. This will occur, for example, when the drill bit is consumable.

Additionally, in certain circumstances multiple "bolt-like" polymer anchors could be used to attach a region of soft tissue to bone, rather than using a row of connected stitches.

Moreover, while the endoscopic procedures described above are generally preferred over open procedures because the endoscopic procedures are less invasive, similar techniques can be used in an open surgery environment if desired.

Further, while thermoplastic polymers have been discussed above, the polymer may be delivered in liquid, non-molten form and cured or dried in situ. For example, the polymer may be a thermoset polymer, e.g., a UV or laser curable material, may be electrolytic gelling, or may be in the form of a hydrogel (e.g., pH sensitive or ionic sensitive), a pluronic, or a sol-gel system, e.g. a polxamer polyol.

Moreover, non-polymeric flowable materials may be used in place of the polymer, e.g., injectable bone cements such as polyacrylic acid/divalent metal ion cements.

What is claimed is:

1. A method of anchoring soft tissue to bone comprising:
   piercing the soft tissue;
   forming an opening in an underlying area of the bone;
   delivering a material, in a flowable state, to the opening; and
   molding a portion of the material that is not in the opening to form a fixation device constructed to hold the soft tissue in place against the bone after the material changes state to a relatively less flowable state.

2. The method of claim 1 wherein the molding step includes forming a portion of the material into a shape that extends radially over a portion of the soft tissue surrounding the opening.

3. The method of claim 2 wherein the formed portion extending radially over the soft tissue is coextensive with the material in the opening, defining a bolt-like anchor.

4. The method of claim 1 wherein the forming step includes drilling or abrading.

5. The method of claim 1 wherein all of the steps are performed endoscopically.

6. The method of claim 1 further comprising incorporating bone fragments generated during the forming step into the material during or prior to the delivering step.

7. The method of claim 1 wherein the material comprises an osteoconductive filler.

8. The method of claim 1 further comprising causing the material to infiltrate the trabecular network.

9. The method of claim 1 wherein the opening has a diameter of less than about 3 mm.

10. The method of claim 1 wherein the opening has a diameter of from about 0.1 to 6.0 mm.

11. The method of claim 1 wherein the forming step is performed using micro-tooling.

12. The method of claim 1 wherein the material comprises a polymer.

13. A method of fixing soft tissue to bone comprising:
    (a) at a first location, piercing through the soft tissue;
    (b) forming an opening in the bone underlying the soft tissue;
    (c) delivering a fixation device through the pierced tissue to the opening;
    (d) delivering a material, in a non-liquid state, to the vicinity of the opening; and
    (e) after delivery, liquifying and subsequently resolidifying the material to anchor at least a portion of the fixation device in the opening.

14. The method of claim 13, wherein said fixation device is selected from the group consisting of suture, anchors and screws.

15. The method of claim 14 wherein said fixation device is a suture.

16. The method of claim 15, further comprising:
    (f) drawing the suture across the soft tissue to a second location, and
    (g) repeating steps (a)–(e) at the second location to form a stitch with said suture between the first and second locations, the stitch securing the soft tissue to the bone.

17. The method of claim 16 further comprising, after step (g), (h) cutting the suture.

18. The method of claim 17 comprising performing steps (a) and (h) with a single tool.

19. The method of claim 16 further comprising repeating steps (f)–(g) at subsequent locations to form a line of connected stitches.

20. The method of claim 15 comprising delivering the suture as a continuous length from a supply of suture material.

21. The method of claim 13 further comprising gripping the soft tissue to hold it in place against the bone.

22. The method of claim 13 further comprising performing steps (a)–(d) endoscopically.

23. The method of claim 13 comprising performing steps (c) and (d) substantially simultaneously.

24. The method of claim 13 comprising performing step (c) prior to step (d).

25. The method of claim 13 comprising providing said material in the form of a pellet, powder, chips, flakes or rod, and further comprising melting the material prior to delivery.

26. The method of claim 13 further comprising incorporating bone fragments generated during the forming step into the material during or prior to the delivering step.

27. The method of claim 13 further comprising incorporating an osteoconductive filler into said material.

28. The method of claim 27 wherein the opening has a diameter of from about 0.1 to 6.0 mm.

29. The method of claim 13 further comprising causing the material, in its flowable state, to infiltrate the trabecular network.

30. The method of claim 13 wherein the forming step comprises forming a opening having a diameter of less than about 3 mm.

31. The method of claim 13 wherein the forming step comprises drilling or abrading.

32. The method of claim 13 further comprising performing the forming step using micro-tooling.

33. The method of claim 13 wherein the method comprises performing the forming step in the bone of a human shoulder.

34. The method of claim 33 wherein the method comprises a rotator cuff repair.

35. A surgical instrument for tissue fixation comprising:
    a handpiece constructed to be held by a surgeon during a fixation procedure; and
    a fixation instrument, mounted on the handpiece and comprising a cannulated tube defining a lumen;

a piercing element constructed to be delivered through the lumen, to pierce through bone and form an opening therein;

a delivery device for delivering a flowable material and a fixation device through the lumen to the opening; and a heating element for heating said material to a molten state.

36. The surgical instrument of claim 35 wherein the fixation device comprises a suture.

37. The surgical instrument of claim 36 further comprising a suture feed mechanism constructed to deliver the suture through the lumen to the opening.

38. The surgical instrument of claim 37 further comprising a probe configured to be positioned, in use, adjacent the opening, and constructed to move in a direction generally perpendicular to the direction of travel of suture material between a first attachment location and a second attachment location to tighten a stitch formed between the two locations with the suture.

39. The surgical instrument of claim 38 wherein said probe is mounted on an external surface of said fixation instrument.

40. The surgical instrument of claim 39 wherein said probe is constructed to be manually actuated by a surgeon during an endoscopic procedure.

41. The surgical instrument of claim 37 further comprising a drive mechanism constructed to drive the piercing element and the suture feed mechanism.

42. The surgical instrument of claim 41 further comprising a clutch mechanism constructed to allow a surgeon to selectively engage and disengage the drive of the piercing element and the drive of the suture feed mechanism.

43. The surgical instrument of claim 36 wherein said piercing element is constructed to cut said suture.

44. The surgical instrument of claim 35 further comprising a drive mechanism constructed to drive the piercing element.

45. The surgical instrument of claim 44 or 41 wherein the drive mechanism is disposed in said handpiece.

46. The surgical instrument of claim 35 wherein the surgical instrument is constructed for endoscopic use.

47. The surgical instrument of claim 35 wherein said heating element is mounted on said fixation instrument.

48. The surgical instrument of claim 37 wherein said suture feed mechanism comprises a movable needle positioned to be advanced at least partially into the lumen to feed the suture towards the opening.

49. The surgical instrument of claim 35 wherein said handpiece comprises a reservoir for receiving the material in solid form.

50. The surgical instrument of claim 49 wherein said reservoir is constructed to receive a supply of pellets of the material and said handpiece further comprises a mechanism for delivering said pellets from said reservoir to said lumen.

51. The surgical instrument of claim 49 wherein said reservoir is constructed to receive a supply of powdered material and said handpiece further comprises a mechanism for delivering a predetermined dose of powdered material from said reservoir to said lumen.

52. The surgical instrument of claim 35, wherein said fixation instrument is detachable from said handpiece.

53. The surgical instrument of claim 35 further comprising a mixing device, within the lumen, constructed to mix bone fragments and debris generated during opening forming into the material prior to delivery to the opening.

54. The surgical instrument of claim 35 further comprising a reservoir for receiving supply of the material.

55. The surgical instrument of claim 35 wherein said handpiece is constructed to receive attachments other than said fixation instrument.

56. The surgical instrument of claim 35 wherein said fixation instrument is constructed to perform a complete fixation procedure without removing the fixation instrument from the surgical site.

57. The surgical instrument of claim 35 wherein the delivery device is constructed to deliver the material in a flowable state.

58. A method of securing a first layer of soft tissue to a second layer of soft tissue comprising:

forming an opening extending through both layers of soft tissue;

delivering a material, in a flowable state, through the opening so that the flowable material extends beyond the soft tissue at each end of the opening; and causing the material to change state, to a relatively less flowable state, forming an anchor to secure the two layers of soft tissue together.

59. A method of securing a fixation device within an opening in a tissue, comprising:

forming an opening in the tissue using a consumable cutting tool;

delivering a material in a flowable state to said opening, the delivery comprising causing the cutting tool to melt in response to frictional heat generated during the forming step; and changing the state of the material so that the material forms an interference fit that secures the fixation device in the opening.

60. The method of claim 59 wherein said tissue comprises bone.

61. The method of claim 59 wherein said tissue comprises soft tissue.

62. The method of claim 59 wherein said fixation device is selected from the group consisting of suture, anchors, and screws.

63. The method of claim 59 wherein the changing step comprises allowing the material to at least partially harden.

64. The method of claim 59 wherein the changing step comprises at least partially cross-linking the material.

65. The method of claim 1 wherein said material comprises a polymer.

66. The method of claim 65 wherein said polymer comprises a thermoplastic polymer.

67. The method of claim 59 wherein said material comprises a hydrogel.

68. The method of claim 59 further comprising using the fixation device to secure a second tissue to the tissue having the opening.

69. The method of claim 68 wherein the tissue having the opening comprises bone and the second tissue comprises soft tissue.

70. The method of claim 69 further comprising, prior to delivery of the material:

piercing the soft tissue;

forming the opening in an underlying area of the bone; and delivering the fixation device through the pierced tissue;

wherein the fixation device is constructed to hold the soft tissue in place against the bone.

71. The method of claim 70 wherein the fixation device comprises a suture.

72. The method of claim 71 wherein the suture includes a region of increased surface area to enhance anchoring.

73. The method of claim 72 wherein said region is selected from the group consisting of knots, barbs, braided areas, balls and shaped elements.

74. The method of claim 70 wherein all of the steps are performed endoscopically.

75. The method of claim 70 further comprising incorporating bone fragments generated during the forming step into the material during or prior to the delivering step.

76. The method of claim 70 further comprising causing the material to infiltrate the trabecular network.

77. The method of claim 59 further comprising incorporating bone fragments into the flowable material during or prior to the delivering step.

78. The method of claim 59 wherein the flowable material includes an osteoconductive filler.

79. The method of claim 59 further comprising causing the flowable material to infiltrate the trabecular network.

80. The method of claim 59 wherein the forming step is performed using micro-tooling.

81. The method of claim 59 wherein the opening has a diameter of less than about 3 mm.

82. The method of claim 59 wherein all of the steps are performed using a single endoscopic surgical tool having a plurality of attachments, and the tool is not removed from the patient until after the steps are completed.

83. A method of securing a fixation device within an opening in a tissue, comprising:
forming an opening in a tissue with a cutting tool having a detachable portion;
detaching the detachable portion in the opening after the forming step is completed, to serve as the fixation device;
delivering a material in a flowable state to said opening; and
changing the state of the material so that the material forms an interference fit that secures the fixation device in the opening.

84. A method of fixing soft tissue to bone comprising:
(a) at a first location, piercing through the soft tissue;
(b) forming an opening in the bone underlying the soft tissue;
(c) delivering a fixation device through the pierced tissue to the opening;
(d) providing a material in the form of a pellet, powder, chips, flakes or rod;
(e) melting the material to a flowable state;
(d) delivering the material to the opening; and
(e) causing the material to change state, to a relatively less flowable state, to anchor at least a portion of the fixation device in the opening.

85. A surgical instrument for tissue fixation comprising:
a handpiece constructed to be held by a surgeon during a fixation procedure; and
a fixation instrument, mounted on the handpiece and comprising
a cannulated tube defining a lumen;
a piercing element constructed to be delivered through the lumen, to pierce through bone and form an opening therein;
a delivery device for delivering a flowable material and a fixation device through the lumen to the opening; and
a heating element for heating said material to a molten state.

86. The instrument of claim 85 wherein said heating element is mounted on said fixation instrument.

87. A surgical instrument for tissue fixation comprising:
a handpiece constructed to be held by a surgeon during a fixation procedure; and
a fixation instrument, mounted on the handpiece and comprising
a cannulated tube defining a lumen;
a piercing element constructed to be delivered through the lumen, to pierce through bone and form an opening therein;
a delivery device for delivering a flowable material and a fixation device comprising a suture through the lumen to the opening; and
a suture feed mechanism constructed to deliver the suture through the lumen to the opening, comprising a movable needle.

88. A surgical instrument for tissue fixation comprising:
a handpiece constructed to be held by a surgeon during a fixation procedure; and
a fixation instrument, mounted on the handpiece and comprising
a cannulated tube defining a lumen;
a piercing element constructed to be delivered through the lumen, to pierce through bone and form an opening therein; and
a delivery device for delivering a flowable material and a fixation device through the lumen to the opening;
said handpiece including a reservoir for receiving a supply of pellets of the material and a mechanism for delivering the pellets from the reservoir to the lumen.

89. A surgical instrument for tissue fixation comprising:
a handpiece constructed to be held by a surgeon during a fixation procedure; and
a fixation instrument, mounted on the handpiece and comprising
a cannulated tube defining a lumen;
a piercing element constructed to be delivered through the lumen, to pierce through bone and form an opening therein;
a delivery device for delivering a flowable material and a fixation device comprising a suture through the lumen to the opening; and
a suture feed mechanism constructed to deliver the suture through the lumen to the opening;
the handpiece including a drive mechanism constructed to drive the piercing element and suture feed mechanism.

90. The instrument of claim 89 further comprising a clutch mechanism constructed to allow a surgeon to selectively engage and disengage the drive of the piercing element and the drive of the suture feed mechanism.

91. A method of securing a tissue to bone, comprising:
forming an opening in the bone at a first location;
delivering a flowable material and a suture to said opening,
allowing the flowable material to at least partially solidify and secure a portion of the suture in the opening,
drawing a free portion of the suture that extends from the secured portion across the soft tissue to a second location;
forming a second opening in the bone at the second location;
delivering a flowable material and a portion of the suture to said second opening; and
allowing the flowable material to at least partially solidify, the suture defining a stitch between the first and second locations.

92. The method of claim 91 further comprising repeating the drawing, forming, delivering and allowing steps at subsequent locations to form a line of connected stitches.

93. The method of claim 91 further comprising feeding the suture as a continuous length from a supply of suture material.

94. The method of claim 91 further comprising melting the flowable material.

95. The method of claim 94 further comprising causing the molten material to infiltrate the trabecular network.

96. The method of claim 91 wherein the flowable material is in the form of a pellet.

97. The method of claim 91 wherein the flowable material comprises a thermoplastic polymer.

98. The method of claim 91 wherein the forming step comprises forming an opening having a diameter of less than about 3 mm.

99. The method of claim 91 wherein the flowable material comprises a hydrogel.

100. A surgical instrument constructed to perform the steps of the method of claim 91 endoscopically.

101. A surgical instrument constructed to perform the steps of the method of claim 13 endoscopically.

102. A method of securing a fixation device within an opening in bone to secure a soft tissue to the bone, comprising:

piercing the soft tissue;

forming the opening in an underlying area of the bone using a consumable cutting tool;

delivering the fixation device through the pierced tissue, the fixation device being constructed to hold the soft tissue in place against the bone;

delivering a material in a flowable state to said opening by causing the cutting tool to melt in response to frictional heat generated during the forming step; and changing the state of the material so that the material forms an interference fit that secures the fixation device in the opening.

* * * * *

UNITED STATES PATENT AND TRADEMARK OFFICE
CERTIFICATE OF CORRECTION

PATENT NO. : 6,620,185 B1
DATED : September 16, 2003
INVENTOR(S) : Adam James et al.

It is certified that error appears in the above-identified patent and that said Letters Patent is hereby corrected as shown below:

Column 20,
Line 40, delete "and further comprising melting the material prior to delivery."
Line 43, delete "the delivering" and, after "step", insert -- (d) --.

Column 22,
Line 44, delete "1" and replace with -- 59 --.

Signed and Sealed this

Twenty-third Day of March, 2004

JON W. DUDAS
*Acting Director of the United States Patent and Trademark Office*